US006258788B1

(12) United States Patent
Schmaljohn

(10) Patent No.: US 6,258,788 B1
(45) Date of Patent: Jul. 10, 2001

(54) DNA VACCINES AGAINST TICK-BORNE FLAVIVIRUSES

(75) Inventor: Connie S. Schmaljohn, Frederick, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/197,218

(22) Filed: Nov. 20, 1998

Related U.S. Application Data
(60) Provisional application No. 60/065,750, filed on Nov. 20, 1997.

(51) Int. Cl.$^7$ .................................................. A61K 39/12

(52) U.S. Cl. ...................... 514/44; 424/204.1; 424/218.1

(58) Field of Search ............................. 424/204.1, 218.1; 435/6, 5; 514/44

(56) References Cited

U.S. PATENT DOCUMENTS

| 5,204,253 | 4/1993 | Sanford . |
| 5,506,125 | 4/1996 | McCabe . |

FOREIGN PATENT DOCUMENTS

| 0691404 | 7/1995 | (EP) . |
| 9519799 | 7/1995 | (WO) . |

OTHER PUBLICATIONS

Colombage, G. et al. (1998) DNA–based and alphavirus–vectored immunisation with PrM and E proteins elicits long–lived and protective immunity against the flavivirus, Murray Valley encephalitis virus. Virology 250, 151–163.
Schmaljohn, C. et al. (1997) Naked DNA vaccines expressing the prM and E genes of Russian spring summer encephalitis virus and Central European encephalitis virus protect mice from homologous and heterologous challenge. J. Virol. 71, 9563–9568.
Konishi, E. et al. (1992) Mice immunized with a subviral particle containing the Japanese encephalitis virus prM/M and E proteins are protected from lethal infection. Virology 188, 714–720.
Pletnev, A. G. et al. (1986) Tick–borne encephalitis virus genome: The nucleotide sequence coding for virion structural proteins. FEBS 200, 317–321.
Wallner, G. et al. (1996) Characterization and complete genome sequences of high– and low–virulence variants of tick–borne encephalitis virus. J. Gen. Virol. 77, 1035–1042.
Schmaljohn et al., Evaluation of Tick–Borne Encephalitis DNA Vaccine in Monkeys. Virology 263:166–174, 1999.
Aberle et al., A DNA Immunization Model Study with Constructs Expressing the Tick–Borne Encephalitis Virus Envelope Protein E in Different Physical Forms. J. Immunol. 163(12):6756–6761, 1999.

Kozak, Marilyn; "The Scanning Model for Translation: An Update", The J. of Cell Biology, vol. 108, Feb. 1989, pp. 229–241.
Heinz, "Characterization of Tick–Borne Encephalitus Virus and Immunogenicity of its Surface Components in Mice", Acta Virol., 21:308–316 (1977).
Hambleton, et al., "Pathogenesis and Immune Response of Vaccinated and Unvaccinated Rhesus Monkeys to Tick–BOrne Encephalitis Virus", Infection and Immunity, Jun. 1983, pp 995–1003.
Iacono–Connors, et al., "Characterization of Langat virus antigenic determinants defined by monoclonal antibodies to E, NS1 and preM and identification of a protective, non–neutralizing preM–specific monoclonal antibody", Virus Research, 43 (1996), pp. 125–136.
Holzmann, et al., "A Single Amino Acid Substitution in Envelope Protein E of Tick–Borne Encephalitis Virus Leads to Attenuation i n the Mouse Model", J. Virology, Oct. 1990, pp. 5156–5159.
Schalich, et al., "Recombinant Subviral Particles from Tick–Borne Encephalitis Virus are Fusogenic and Provide a Model System for Studying Flavivirus Envelope Glycoprotein Functions", J. Virology, Jul. 1996, pp. 4549–4557.
Konishi, et al., "A Highly Attenuated Host Range–RestrictedVaccinia Virus Strain, NYVAC, Encoding the prM, E, and NS1 Genes of Japanese Encephalitis Virus Prevents JEV Viremia in Swine", VIrology, 190, (1992) pp. 454–458.
Konishi and Mason, "Proper Muturation of the Japanese Encephalitis Virus Envelope Glycoprotein Requires Cosynthesis with the Premembrane Protein", J. Virology, Mar. 1997, pp. 1672–1675.
Kunz et al., "Immunogenicity and Reactogenicity of a Highly Purified Vaccine Against Tick–Borne Encephalitus", J. Medical Virology, 6:103–109 (1980).
Holzmann, et al., "Molecular epidemiology of tick–borne encephalitus virus: cross–protection between European and Far Eastern subtypes", Vaccine, 10:345–349 (1992).
Pincus, et al., "Recombinant Vaccinia VIrus Producing the prM and E Proteins of Yellow Fever Virus Protects Mice from Lethal Yellow Fever Encephalitus", Virology 187:290–297 (1992).
Mason et al., "Japanese Encephalitis Virus–Vaccinia Recombinants Produce Particulate Forms of the Structural Membrance Proteins and Induce High Levels of Protection against Lethal JEV Infection", Virology 180:294–305 (1991).
Eisenbraun, et al., "Examination of Parameters Affecting the Elicitation of Humoral Immune Responses by Particle Bombardment–Mediated Genetic Immunization", DNA and Cell Biology, vol. 12, No. 9, 1993, pp. 791–797.

(List continued on next page.)

Primary Examiner—Donna C. Wortman
(74) Attorney, Agent, or Firm—Elizabeth Arwine; Charles H. Harris

(57) ABSTRACT

Particle mediated immunization of tick-borne flavivirus genes confers homologous and heterologous protection against tick borne encephalitis.

11 Claims, 8 Drawing Sheets

OTHER PUBLICATIONS

Fynan et al., "DNA Vaccines: Protective immunizations by parenteral, mucosal, and gene–gun inoculations", PNAS, USA, vol. 90, Dec. 1993, pp. 11478–11782.

Whalen, "DNA Vaccines for Emerging Infectious Diseases: What If?", Emerging Infectious Diseases, vol. 2, No. 3, Jul.–Sep., 1996, pp. 168–175.

Pertmer, et al., "Gene gun–based nucleic acid immunization: elicitation of humoral and cytotoxic T lymphocyte responses following epidermal delivery of nanogram quantities of DNA", Vaccine, vol. 13, No. 15 (1995), pp. 1427–1430.

Rambukkana, et al., "In Situ Behavior of Human Langerhans Cells in Skin Organ Culture," Laboratory Investigation, vol. 73, No. 4, 1995, pp. 521–531.

J.D. Bos, "The Skin as an Organ of Immunity", Clin. Exp. Immunol., 107 (1997), (Suppl. 1), pp. 3–5.

Fuller, et al., "Induction of immunodeficiency virus–specific immune responses in rhesus monkeys following gene gun–mediated DNA vaccination", J. Medical Primatology, 25:236–241 (1996).

Labuda, et al., "Importance of Localized Skin Infection in Tick–Borne Encephalitis Virus Transmission", Virology, 219, (1996), pp. 357–366.

Chu, et al., "Serological Relationships among Viruses in the Hantavirus Genus, Family Bunyaviridae", Virology 198, (1994), pp. 196–204.

Heinz, et al., " A Topological and Functional Model of Epitopes on the Structural Glycoprotein of Tick–Borne Encephaalitis Virus Defined by Monoclonal Antibodies", Virology 126, (1983), pp. 525–537.

Heinz, et al., "Recombinant and virion–derived soluble and particulate immunogens for vaccination against tick–borne encephalitis", Vaccine, vo. 13, No. 17, (1995), pp. 1636–1642.

Khozinsky and Semonov, "In Vivo Inhibition by Intact Mouse Serum of the Activity of the Flavirus–Induced T–Suppressors of Autoreactive T–Lymphocytes", Acta virol., 28:212–217 (1984).

Gajdosaya and Mayer, "Cell–Mediated Immunity in Flavirus Infections. I. Induction of Cytotoxic T Lymphocytes in Mice by an Attenuated Virus From the Tick–Borne Encephalitis Complex and its Group–Reactive Character", Acta Virol. 25:10–18 (1981).

Mayer et al., " Transfer with dialysable transfer of T–lymphocyte cytolytic response to tick–borne encephalitis virus antigen in naive mice", Acta virol. 24:459–463 (1980).

Mayer et al., "Dialysable specific transfer factor in mice immunized with attenuated Langat virus from the tick–borne encephalitis complex: generation, action and quantitative assay", Acta virol., 26:453–465 (1982).

Vargin and Semenov, "Changes of natural killer cell activity in different mouse lines by acute and asymptomatic flavivirus infections", Acta. virol. 30:303–308 (1986).

Lu, et al., "Simian immunodeficiency virus DNA vaccine trial in Macaques", J. Viorology, vol. 70, No. 6, Jun. 1996, pp. 3978–3991.

Kenyon et al., "Infection of Maca radiata with viruses of the tick–borne encephalitis group," Microbial Pathogenesis (1992), 13:399–409.

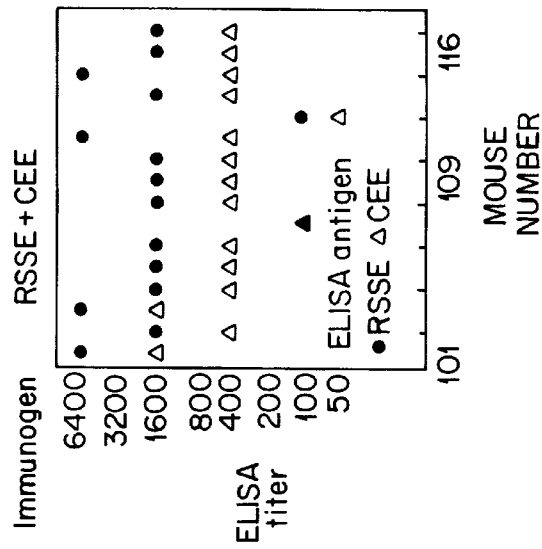
FIG. 4A  FIG. 4B  FIG. 4C
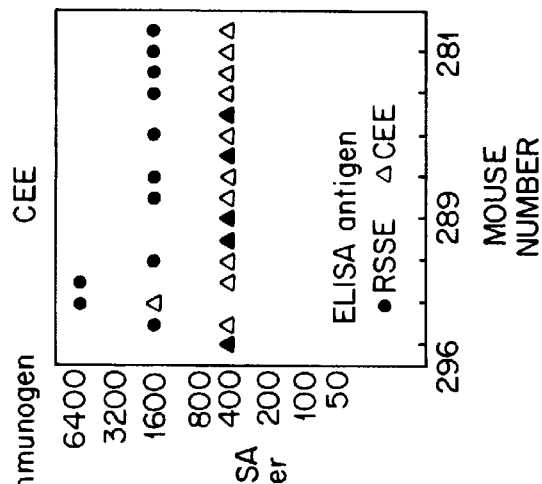
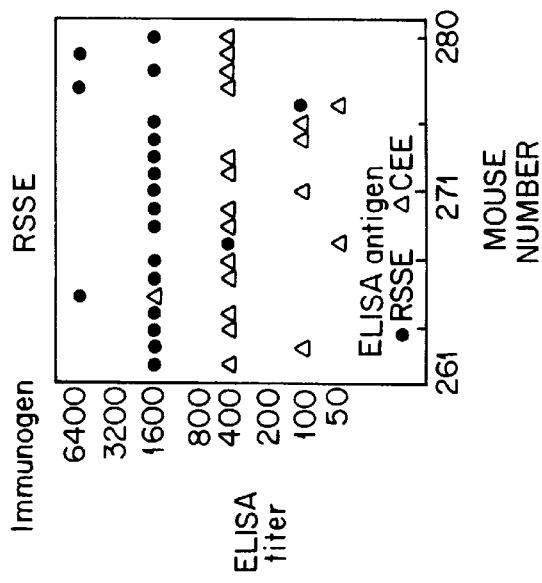

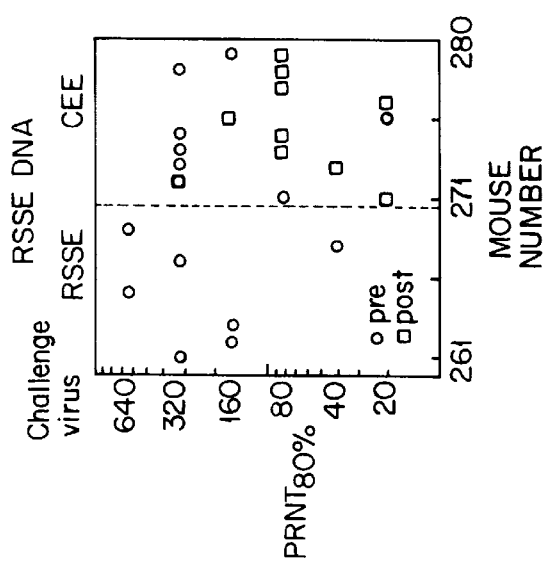
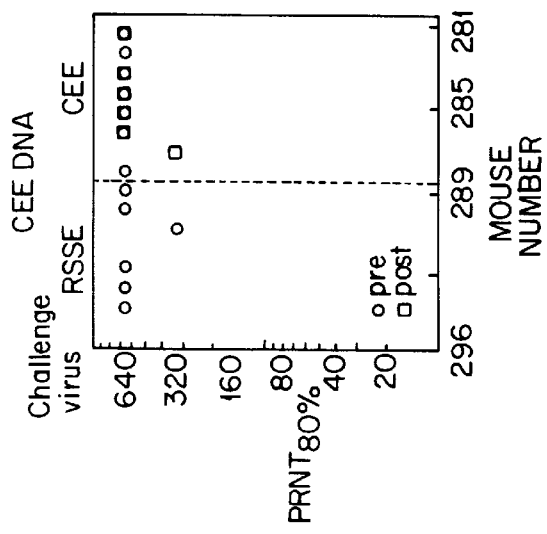
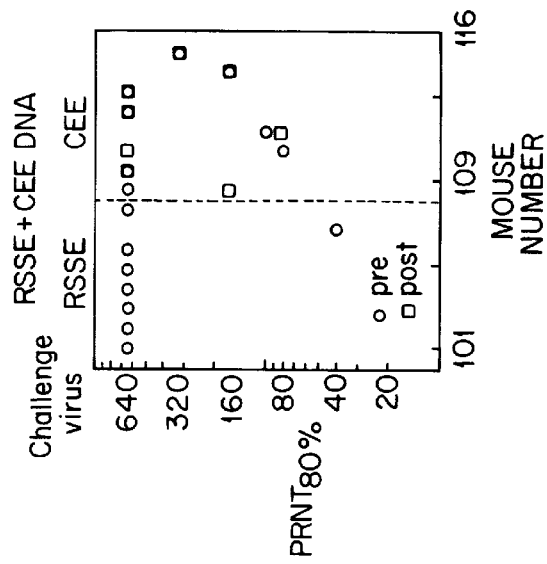

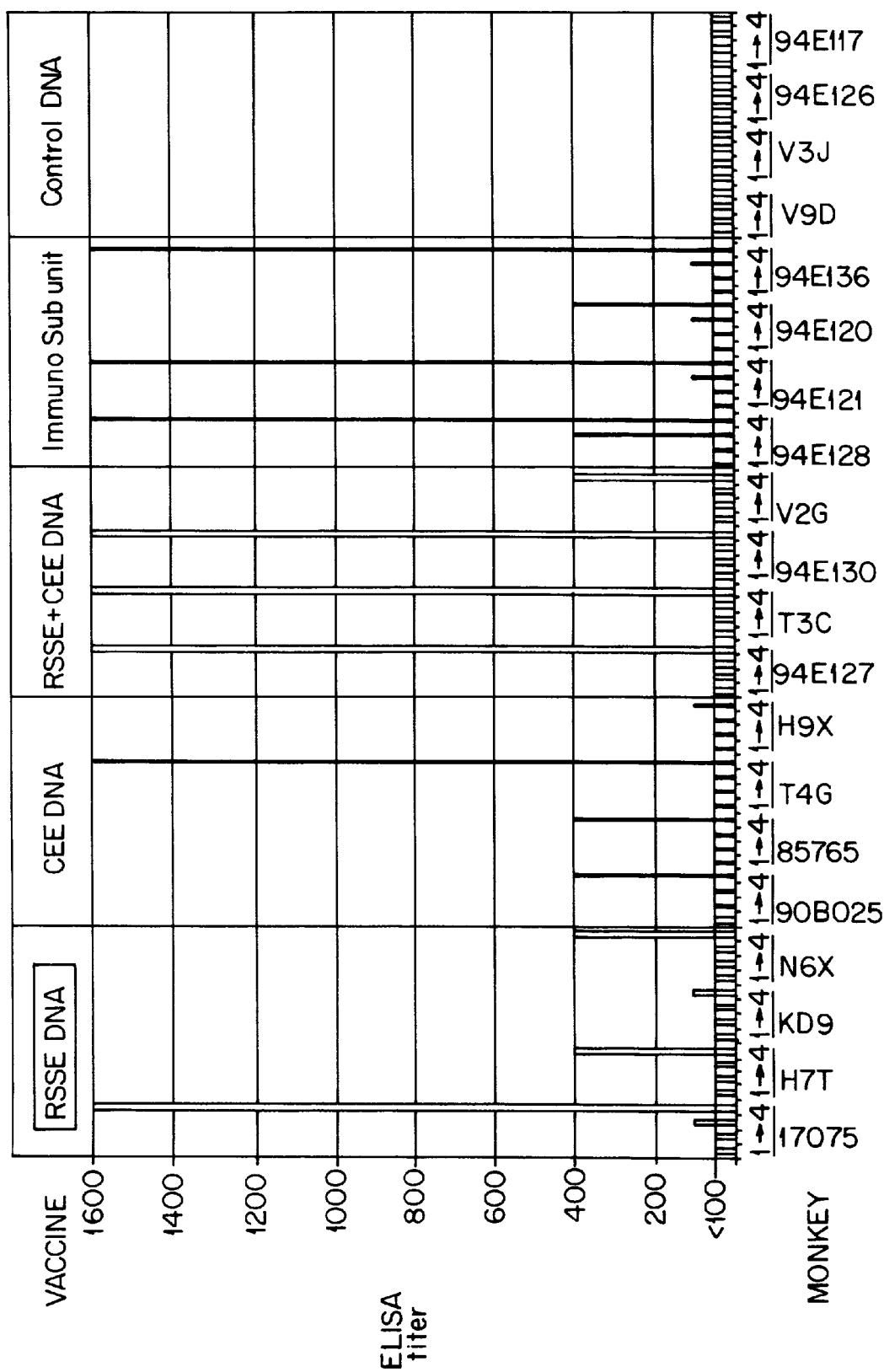

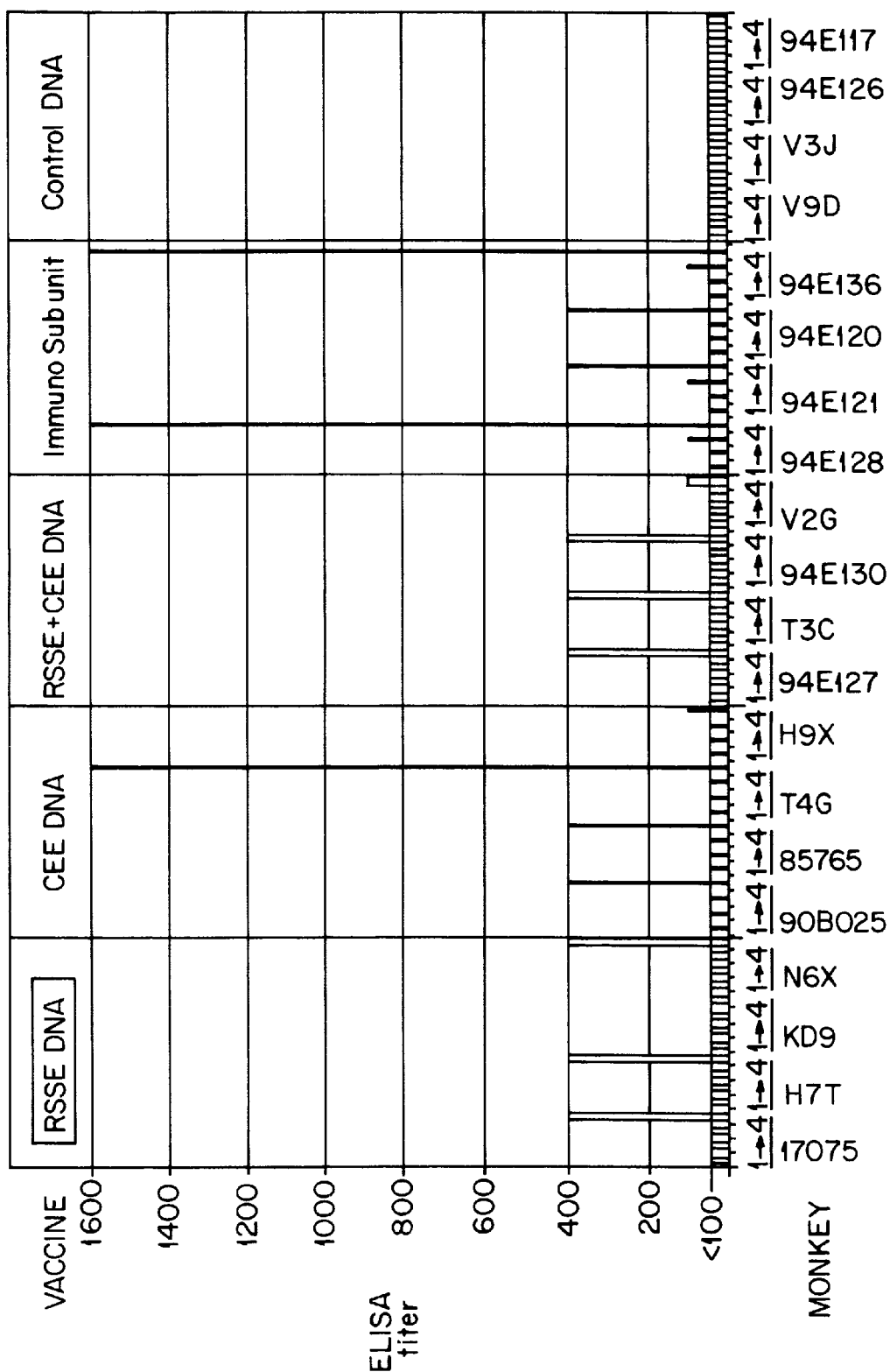

DNA VACCINES AGAINST TICK-BORNE FLAVIVIRUSES

This application claims the benefit of priority under 35 U.S.C. 119(e) of provisional application Ser. No. 60/065,750 filed on Nov. 20, 1997.

Tick-borne encephalitis (TBE) occurs over a wide area of Europe and the former Soviet Union. TBE is most frequently caused by infection with the flaviviruses Central European encephalitis (CEE) virus, or Russian spring summer encephalitis (RSSE) virus. These viruses are antigenically and genetically closely related to one another and often are considered to be subtypes of the same virus. However, two different tick vectors transmit RSSE and CEE viruses (*Ixodes persulcatus* and *Ixodes ricinus*, respectively) and RSSE virus generally causes a more severe disease than does CEE virus (reviewed in Monath, T. P. and F. X. Heinz, 1996, In B. N. Fields et al. (eds.) *Fields Virology*, Third Edition, Lippincott-Raven Publishers: Philadelphia, p. 961).

In parts of Europe, TBE cases have notably declined since the introduction in 1976 of a formalin-inactivated, chick embryo-derived vaccine. The vaccine is based on an Austrian strain of CEE virus, and elicited protective immunity in mice to the homologous CEE virus (strain Hypr) and to four strains of RSSE virus (Holzmann, H. et al., 1992, *Vaccine*, 10, 345). Despite the success of this vaccine, it suffers the disadvantages commonly associated with inactivated virus vaccines such as the requirement for large-scale production and purification of a highly infectious human pathogen, the risk of incomplete inactivation of the virus, and the need to deliver the vaccine with adjuvant in a three-shot series (Kunz, C. F. et al., 1980, *J. Med. Virol.* 6, 103). Also, this vaccine is not licensed for use in U.S. military personnel nor in U.S. travelers to TBE-endemic regions.

For these reasons, there is a need for an improved TBE vaccine.

SUMMARY OF THE INVENTION

The present invention satisfies the need discussed above. In this report, we describe two plasmid-based TBE candidate vaccines, which express the premembrane (prM) and envelope (E) genes of RSSE or CEE viruses under control of a cytomegalovirus early promoter. We chose the prM and E genes for expression because of earlier reports with other flaviviruses which indicated that coexpressed prM and E form subviral particles that are able to elicit neutralizing and protective immune responses in animals (Konishi, E. and P. W. Mason, 1993, *J. Virol.* 67: 1672; Konishi, E. et al., 1992, *Virology* 190:454; Pincus, S. et al., 1992, *Virology* 187: 290). Coexpression of prM and E of CEE virus also produces subviral particles, and although these particles were not tested for immunogenicity, they were found to retain biological properties of complete virus such as membrane fusion and hemagglutination (Schalich, J. et al., 1996, *J. Virol.* 70:4549).

To deliver our DNA vaccines, we chose to use the PowderJect-XR™ gene gun device described in WO 95/19799, Jul. 17, 1995. This instrument, which delivers DNA-coated gold beads directly into epidermal cells by high-velocity particle bombardment, was shown to more efficiently induce both humoral and cell-mediated immune responses, with smaller quantities of DNA, than inoculation of the same DNAs by other parenteral routes (Eisenbraun, M. et al., 1993, *DNA Cell. Biol.* 12: 791; Fynan, E. F. et al., 1993, *Proc. Natl. Acad. Sci. U.S.A.* 90: 11478; Haynes, J. R. et al., 1994, *AIDS Res. Hum. Retroviruses* 10: Suppl. 2:S43; Pertmer, T. M. et al., 1995, *Vaccine* 13: 1427). Epidermal inoculation of the DNA candidate vaccines also offers the advantages of gene expression in an immunologically active tissue that is generally exfoliated within 15 to 30 days, and which is an important natural focus of viral replication after tick-bite (Bos, J. D., 1997, *Clin. Exp. Immunol.* 107 Suppl. 1:3; Labuda, M. et al., 1996, *Virology* 219:357; Rambukkana, A. et al., 1995, *Lab. Invest.* 73:521; Stingl, G., 1993, *Recent Results Cancer Res.* 128:45). In this application we describe the elicitation of cross-protective immunity to RSSE and CEE viruses by DNA vaccines.

Therefore, the present invention relates to a method for eliciting in an individual an immune response against an alphavirus which causes tick-borne encephalitis comprising delivering to the individual a DNA vaccine comprising a vector including a viral antigen such that when the antigen is introduced into a cell from the individual, the DNA is expressed, the viral antigen is produced in the cell and an immune response against the antigen is mounted.

In one aspect of the invention, the DNA vaccine is delivered by coating a small carrier particle with the DNA vaccine and delivering the DNA-coated particle into an animal's epidermal tissue via particle bombardment. This method may be adapted for delivery to either epidermal or mucosal tissue, or delivery into peripheral blood cells, and thus may be used to induce humoral, cell-mediated, and secretory immune reponses in the vaccinated individual.

The DNA vaccine according to the present invention is inherently safe, is not painful to administer, and should not result in adverse side effects to the vaccinated individual. In addition, the invention does not require growth or use of tick-borne flavivirus, which may be spread by aerosol transmission and are typically fatal.

BRIEF DESCRIPTION OF THE DRAWINGS

These and other features, aspects, and advantages of the present invention will become better understood with reference to the following description, appended claims, and accompanying drawings where:

Figure 1:
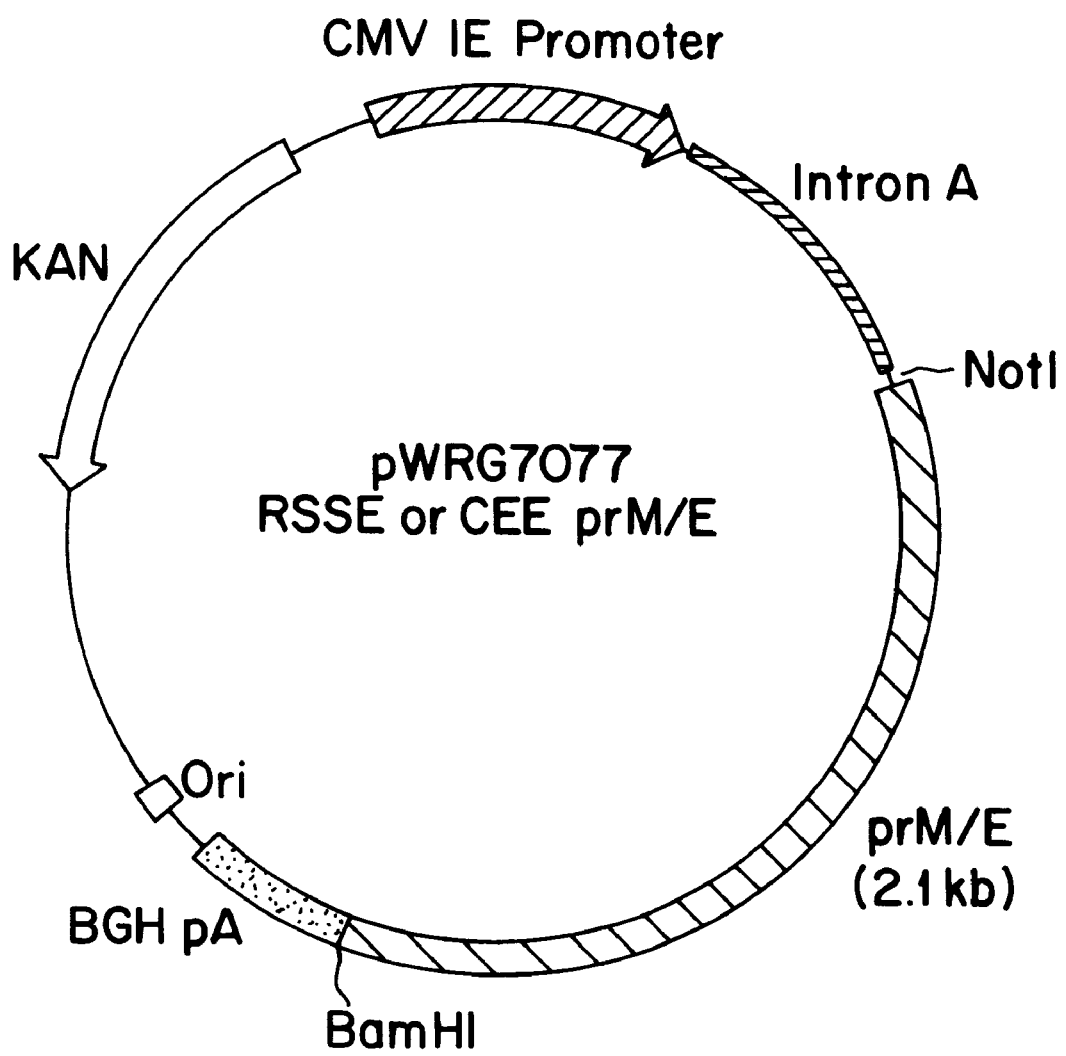
FIG. 1. Schematic of pWRG7077 containing prM and E genes of RSSE and CEE viruses which were amplified by RT-PCR and cloned into NotI and BamHI sites of pWRG7077 (PowderJect Vaccines, Inc., Madison, Wisc.). Characteristics of pWRG7077 are similar to those of pWRG1602 described previously (Dimmock, N. J., 1995, *Med. Virol.* 5: 165) and include a human cytomegalovirus early promoter (CMV IE promoter) and intron A, a bovine growth hormone transcription terminator and polyadenylation signal (BGH pA), and a kanamycin resistance gene.

A. Mice were immunized two times, 4 wk apart, with 1 µg/dose of pJW4303 expressing the prM and E genes of RSSE. ELISA was performed on RSSE antigen-coated plates using sera collected just before the second immunization (1 vacc) or 4 wk after the second immunization (2 vacc).

B. Mice were immunized once with 1 µg of pJW4303 expressing the RSSE prM and E genes and, 4 wk later, were immunized once with 1 µg of pWRG7077 expressing the RSSE prM and E genes. ELISA was performed on RSSE or CEE antigen-coated plates using sera collected 4 wk after the second immunization. Controls for each experiment were comparable plasmids with no gene insert.

FIGS. 4A, B and C. ELISA titers to RSSE and CEE of mice immunized with RSSE (FIG. 4A), CEE (FIG. 4B), or RSSE and CEE (FIG. 4C) DNAs. Mice were immunized three times at 4-wk intervals with 0.5 µg DNA/dose. Titers of sera were determined 4 wk after the final immunization.

FIGS. 5A, B and C. Plaque reduction neutralization by pre- and postchallenge sera of mice immunized with naked DNA vaccines expressing the prM and E genes of RSSE (FIG. 5A), CEE (FIG. 5B) or RSSE and CEE (FIG. 5C) viruses. Twofold dilutions of sera from 1:20 to 1:640 were used in PRNT with CEE virus. PRNT titers are listed as the greatest dilution of serum which resulted in $\geq 80\%$ reduction of the number of plaques observed in controls incubated with serum from mice vaccinated with control plasmids.

Figures 6A, 6B, 6C:
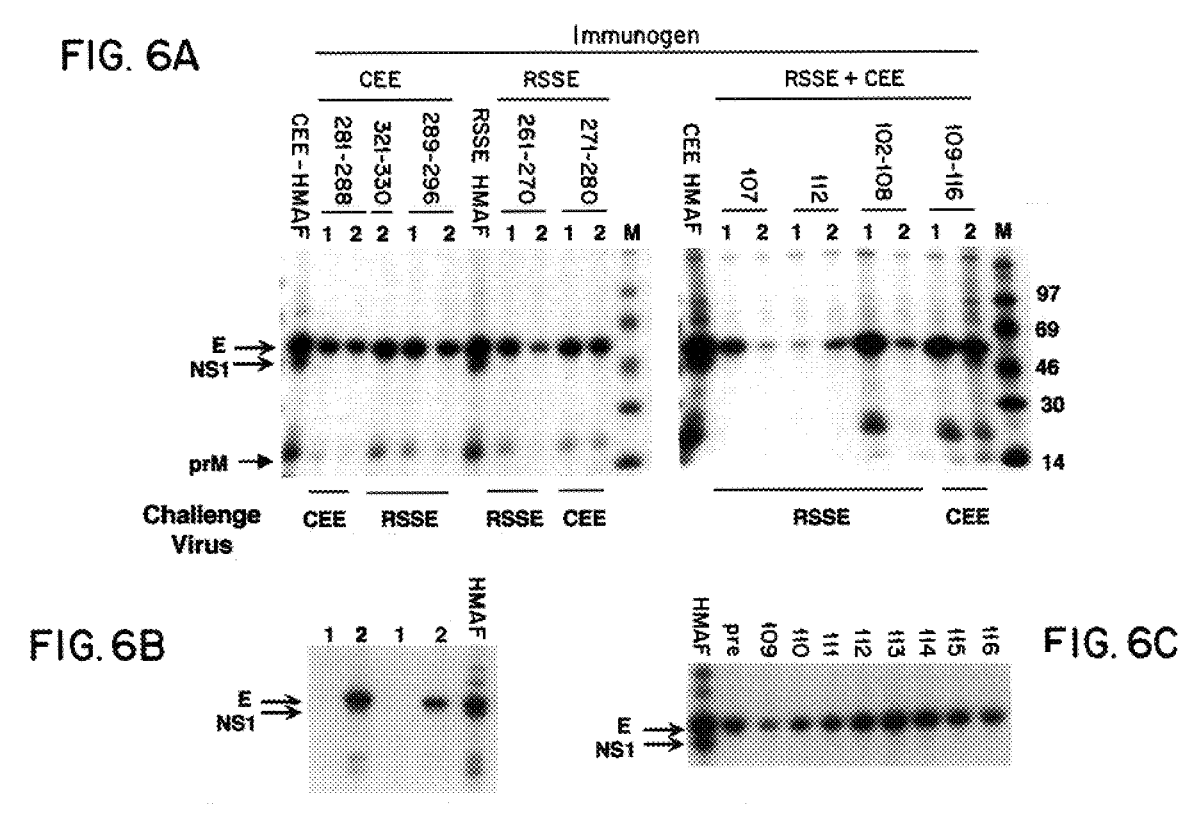

FIGS. 6A–C. Immune precipitation of radiolabeled Langat virus proteins with pre- (lanes 1) and postchallenge (lanes 2) sera from mice vaccinated with naked DNA vaccines expressing the prM and E genes of CEE, RSSE or RSSE and CEE viruses. Immune precipitation products were analyzed by PAGE and autoradiography. Control sera were hyperimmune mouse ascitic fluids (HMAF) to authentic RSSE or CEE viruses. The mouse numbers shown above each autoradiograph correspond to those in FIG. 4 and FIG. 5.

A. Immune precipitation results obtained with pooled sera, except for those labeled 107 and 112, which are individually analyzed serum samples.

B. Immune precipitation results using sera from the two controls that survived challenge with CEE virus.

C. Immune precipitation results from individual sera in group 109–116. The sizes (kD) of molecular weight markers (M) are indicated.

FIGS. 7A and B. Monkey ELISA titers on RSSE (FIG. 7A) and CEE (FIG. 7B) antigen after three immunizations.

DETAILED DESCRIPTION

In this application is described a composition and method for the vaccination of individuals against tick-borne encephalitis. The method comprises delivery of a DNA encoding an antigen to cells of an individual such that the antigen is expressed in the cell and an immune response is induced in the individual.

DNA vaccination mimics the de novo antigen production and MHC class I-restricted antigen presentation obtainable with live vaccines, without the risks of pathogenic infection. DNA vaccination involves administering antigen-encoding polynucleotides in vivo to induce the production of a correctly folded antigen(s) within the target cells. The introduction of the DNA vaccine will cause to be expressed within those cells the structural protein determinants associated with the pathogen protein or proteins. The processed structural proteins will be displayed on the cellular surface of the transfected cells in conjunction with the Major Histocompatibility Complex (HMC) antigens of the normal cell. Even when cell-mediated immunity is not the primary means of preventing infection, it is likely important for resolving established infections. Furthermore, the structural proteins released by the expressing transfected cells can also be picked up by antigen-presenting cells to trigger systemic humoral antibody responses.

This vaccine approach is advantageous over subunit vaccines which do not elicit a cytotoxic response necessary to prevent the establishment of infection or disease. Also, this DNA vaccine approach allows delivery to mucosal tissues which may aid in conferring resistance to viral introduction since entry of the virus may be through mucosal tissues.

In order to achieve the immune response sought, a DNA vaccine construct capable of causing transfected cells of the vaccinated individual to express one or more major viral antigenic determinant is necessary. This can be done by identifying regions of the viral genome which code for viral glycoproteins, and joining such coding sequences to promoters capable of expressing the sequences in cells of the vaccinee. Alternatively, the viral genome itself, or parts of the genome, can be used.

In one embodiment, the present invention relates to a DNA or cDNA segment which encodes an antigen from a tick-borne flavivirus such as RSSE, CEE, or Langat. More specifically, prM and E genes of CEE were deduced from the CEE viral genome sequence available in Genbank at accession U39292 (Wallner, G. et al., 1996, *J. Gen. Virol.* 77, 1035–1042) and from RSSE available in Genbank at accession X03870 (Pletnev, A. G. et al., 1986, *FEBS Lett.* 22, 317–321). For CEE, this corresponds to nucleotides 424–2478 (specified in SEQ ID NO:1) of the 10,835 bp genome in Genbank U39292 and the same region was amplified for RSSE, strain Sofjin, but since only a partial gene sequence is available in Genbank, the region amplified corresponds to 419–2470 (specified as SEQ ID NO:2) of the 3,697 bp sequence reported in Genbank X03870. The nucleotide sequences of the amplified regions are about 81% identical. The deduced amino acid sequences are about 94% identical.

DNA or polynucleotide sequences to which the invention also relates include fragments of prM and E containing protective epitopes or antigenic determinants. PrM and E can be delivered in noncontiguous sequences, however, it is preferable that PrM and E be delivered together to get the best results in terms of folding of the proteins and assurance that both proteins are expressed in the same cells.

The derived sequence is not necessarily physically derived from the nucleotide sequence shown in SEQ ID NO:1 or SEQ ID NO:2, but may be generated in any manner, including for example, chemical synthesis or DNA replication or reverse transcription or transcription, which are based on the information provided by the sequence bases in the region(s) from which the polynucleotide is derived. In addition, combinations of regions corresponding to that of the designated sequence may be modified in ways known in the art to be consistent with an intended use. The sequences of the present invention can be used in diagnostic assays such as hybridization assays and polymerase chain reaction (PCR) assays for the detection of TBE.

The exemplified fragments were obtained using reverse transcription and PCR amplification of a portion of genomic RNA using specific oligonucleotide primers designed to correspond to sequences previously reported for CEE and RSSE viruses (Genbank U39292, X03870, respectively). For the forward primers, nucleotides were modified around the translation initiation codon (bold type below) to generate sequences with a favorable context for translation initiation (Kozak, M., 1989, *J. Cell. Biol.* 108:229). The forward and reverse primers for RSSE were: 5'GCAGTAGACAG-GATGGGTTGGTTG3' (SEQ ID NO:3) and 5'GCACAGC-CAACTTAAGCTCCCACTCC3' (SEQ ID NO:4). The forward and reverse primers for CEE virus were:

5'GCGACGGACAGGATGGGCTGGTTGCTAG3' (SEQ ID NO:5), and 5'CACAGCGCAGCCAACTTACGC-CCCCACTCC3' (SEQ ID NO:6). Primers can include additional non-complimentary sequences that are fixed during amplification to facilitate subsequent cloning.

It is understood in the art that certain changes to the nucleotide sequence employed in a genetic construct have little or no bearing on the proteins encoded by the construct. Such changes result either from silent point mutations or point mutations that encode different amino acids that do not appreciably alter the behavior of the encoded protein. It is also understood that portions of the coding region can be eliminated without affecting the ability of the construct to achieve the desired effect, namely induction of a protective immune response against tick-borne flavivirus challenge. It is further understood in the art that certain advantageous steps can be taken to increase the antigenicity of an encoded protein by modifying its amino acid composition. Such changes in amino acid composition can be introduced by modifying the genetic sequence encoding the protein. It is contemplated that all such modifications and variations of the tick-borne flavivirus glycoprotein genes are equivalents within the scope of the present invention.

The DNA encoding the desired antigen can be introduced into the cell in any suitable form including, a linearized plasmid, a circular plasmid, a plasmid capable of replication, an episome, RNA, etc. Preferably, the gene is contained in a plasmid. In a particularly preferred embodiment, the plasmid is an expression vector. Individual expression vectors capable of expressing the genetic material can be produced using standard recombinant techniques.

Therefore, in another embodiment, the present invention relates to a recombinant DNA molecule that includes a vector and a DNA sequence as described above. The vector can take the form of a plasmid such as pCRII (Invitrogen) or pJW4303 (Konishi, E. et al., 1992, *Virology* 188:714), or any expression vector such as viral vectors e.g. adenovirus or Venezuelan equine encephalitis virus and others known in the art. Preferably, a promoter sequence operable in the target cells is operably linked to the DNA sequence. Several such promoters are known for mammalian systems which may be joined 5', or upstream, of the coding sequence for the encoded protein to be expressed. A suitable promoter is the human cytomegalovirus immediate early promoter. A downstream transcriptional terminator, or polyadenylation sequence, such as the polyA addition sequence of the bovine growth hormone gene, may also be added 3' to the protein coding sequence.

A suitable construct for use in the method of the present invention is pWRG7077 (4326 bp)(PowderJect Vaccines, Inc., Madison, Wisc.), FIG. 1. pWRG7077 includes a human cytomegalovirus (hCMV) immediate early promoter and a bovine growth hormone polyA addition site. Between the promoter and the polyA addition site is Intron A, a sequence that naturally occurs in conjunction with the hCMV IE promoter that has been demonstrated to increase transcription when present on an expression plasmid. Downstream from Intron A, and between Intron A and the polyA addition sequence, are unique cloning sites into which the prM/E DNA can be cloned. Also provided on pWRG7077 is a gene that confers bacterial host-cell resistance to kanamycin. Any of the fragments that encode RSSE or CEE proteins can be cloned into one of the cloning sites in pWRG7077, using methods known to the art.

In a further embodiment, the present invention relates to host cells stably transformed or transfected with the above-described recombinant DNA construct. The host cell can be prokaryotic such as Bacillus or *E. coli*, or eukaryotic such a Saccharomyces or Pichia, or mammalian cells or insect cells. The vector containing the RSSE or CEE sequence is expressed in the bacteria and the expressed product used for diagnostic procedures or as a vaccine. Please see e.g., Maniatis et al., 1985 *Molecular Cloning: A Laboratory Manual* or *DNA Cloning*, Vol. I and II (D. N. Glover, ed., 1985) for general cloning methods. The DNA sequence can be present in the vector operably linked to a highly purified IgG molecule, an adjuvant, a carrier, or an agent for aid in purification of RSSE or CEE proteins. The transformed or transfected host cells can be used as a source of DNA sequences described above. When the recombinant molecule takes the form of an expression system, the transformed or transfected cells can be used as a source of the protein encoded by the DNA. The DNA can be used as circular or linear, or linearized plasmid as long as the CEE and RSSE sequences are operably linked to a promoter which can be expressed in the transfected cell.

In the present invention, the DNA vaccine is transferred into the susceptible individual by means of an accelerated particle gene transfer system. The technique of accelerated particles gene delivery is based on the coating of DNA to be delivered into cells onto extremely small carrier particles, which are designed to be small in relation to the cells sought to be transformed by the process. The DNA sequence containing the desired gene can be simply dried onto a small inert particle. The particle may be made of any inert material such as an inert metal (gold, silver, platimun, tungsten, etc.) or inert plastic (polystyrene, polypropylene, polycarbonate, etc.). Preferably, the particle is made of gold, platinum or tungsten. Most preferably the particle is made of gold. Suitably, the particle is spherical and has a diameter of 0.5 to 5 microns, preferably 1 to 3 microns.

The DNA sequence containing the desired gene prepared in the form suitable for gene introduction can be simply dried onto naked gold or tungsten pellets. However, DNA molecules in such a form may have a relatively short period of stability and may tend to degrade rather rapidly due to chemical reactions with the metallic or oxide substrate of the particle itself. Thus, if the carrier particles are first coated with an encapsulating agent, the DNA strands have greatly improved stability and do not degrade significantly even over a time period of several weeks. A suitable encapsulating agent is polylysine (molecular weight 200,000) which can be applied to the carrier particles before the DNA molecules are applied. Other encapsulating agents, polymeric or otherwise, may also be useful as similar encapsulating agents, including spermidine. The polylysine is applied to the particles by rinsing the gold particles in a solution of 0.02% polylysine and then air drying or heat drying the particles thus coated. Once the metallic particles coated with polylysine were properly dried, DNA strands are then loaded onto the particles.

The DNA is loaded onto the particles at a rate of between 3 and 30 micrograms of DNA per milligram of gold bead spheres. The preferable ratio of DNA to gold is 0.5–5.0 ug of DNA per milligram of gold. A sample procedure begins with gamma irradiated tefzel tubing. The gold is weighed out into a microfuge tube, spermidine (free base) at about 0.05 M is added and mixed, and then the DNA is added. A 10% CaCl solution is incubated along with the DNA for about 10 minutes to provide a fine calcium precipitate. The precipitate carries the DNA with it onto the beads. The tubes are microfuged and the pellet resuspended and washed in 100% ethanol and the final product resuspeded in 100% ethanol at 0.0025 mg/ml PVP. The gold with the DNA is then applied onto the tubing and dried.

The general approach of accelerated particle gene transfection technology is described in U.S. Pat. No. 4,945,050 to Sanford. An instrument based on an improved variant of that approach is available commercially from PowderJect Vaccines, Inc., Madison Wisc., and is described in WO 95/19799. All documents cited herein supra and infra are hereby incorporated in their entirety by reference thereto. Briefly, the DNA-coated particles are deposited onto the interior surface of plastic tubing which is cut to a suitable length to form sample cartridges. A sample cartridge is placed in the path of a compressed gas (e.g., helium at a pressure sufficient to dislodge the particles from the cartridge e.g., 350–400 psi). The particles are entrained in the gas stream and are delivered with sufficient force toward the target tissue to enter the cells of the tissue. Further details are available in the published apparatus application.

The coated carrier particles are physically accelerated toward the cells to be transformed such that the carrier particles lodge in the interior of the target cells. This technique can be used either with cells in vitro or in vivo. At some frequency, the DNA which has been previously coated onto the carrier particles is expressed in the target cells. This gene expression technique has been demonstrated to work in prokaryotes and eukaryotes, from bacteria and yeasts to higher plants and animals. Thus, the accelerated particle method provides a convenient methodology for delivering genes into the cells of a wide variety of tissue types, and offers the capability of delivering those genes to cells in situ and in vivo without any adverse impact or effect on the treated individual. Therefore, the accelerated particle method is also preferred in that it allows a DNA vaccine capable of eliciting an immune response to be directed both to a particular tissue, and to a particular cell layer in a tissue, by varying the delivery site and the force with which the particles are accelerated, respectively. This technique is thus particularly suited for delivery of genes for antigenic proteins into the epidermis.

A DNA vaccine can be delivered in a non-invasive manner to a variety of susceptible tissue types in order to achieve the desired antigenic response in the individual. Most advantageously, the genetic vaccine can be introduced into the epidermis. Such delivery, it has been found, will produce a systemic humoral immune response.

To obtain additional effectiveness from this technique, it may also be desirable that the genes be delivered to a mucosal tissue surface, in order to ensure that mucosal, humoral and cellular immune responses are produced in the vaccinated individual. There are a variety of suitable delivery sites available including any number of sites on the epidermis, peripheral blood cells, i.e. lymphocytes, which could be treated in vitro and placed back into the individual, and a variety of oral, upper respiratory, and genital mucosal surfaces.

Gene gun-based DNA immunization achieves direct, intracellular delivery of DNA, elicits higher levels of protective immunity, and requires approximately three orders of magnitude less DNA than methods employing standard inoculation.

Moreover, gene gun delivery allows for precise control over the level and form of antigen production in a given epidermal site because intracellular DNA delivery can be controlled by systematically varying the number of particles delivered and the amount of DNA per particle. This precise control over the level and form of antigen production may allow for control over the nature of the resultant immune response.

The term transfected is used herein to refer to cells which have incorporated the delivered foreign DNA vaccine, whichever delivery technique is used.

It is herein disclosed that when inducing cellular, humoral, and protective immune repsonses after DNA vaccination the preferred target cells are epidermal cells, rather than cells of deeper skin layers such as the dermis. Epidermal cells are preferred recipients of DNA vaccines because they are the most accessible cells of the body and may, therefore, be immunized non-invasively. Secondly, in addition to eliciting a humoral immune response, DNA immunized epidermal cells also elicit a cytotoxic immune response that is stronger than that generated in subepidermal cells. Delivery to epidermis also has the advantages of being less invasive and delivering to cells which are ultimately sloughed by the body.

Although it can be desirable to induce an immune response by delivering genetic material to a target animal, merely demonstrating an immune response is not necessarily sufficient to confer protective advantage on the animal. What is important is to achieve a protective immune response that manifests itself in a clinical difference. That is, a method is effective only if it reduces the severity of the disease symptoms. It is preferred that the immunization method be at least 20% effective in preventing death in an immunized population after challenge with RSSE or CEE. More preferably, the vaccination method is 50% or more effective, and most preferably 70–100% effective, in preventing death in an immunized population. The vaccination method is shown herein to be 100% effective in the mouse model for TBE. Mice have been used extensively as the laboratory model of choice for assessment of protective immune responses to tick-borne flaviviruses (Gajdosova, E. et al., 1981, *Acta Virol.* 25:10; Heinz, F. X. and C. Kunz, 1982, *J. Biol. Stand.* 10:25; Holzmann, H. et al., 1990, *J. Virol.* 64:5156; Khozinsky, V. V. and B. F. Semenov, 1984, *Acta Virol.* 28:212; Mayer, V. E. et al., 1980,. *Acta Virol.* 24:459; Mayer, V. E. et al., 1982, *Acta Virol.* 26:453; Semenov, B. F. et al., 1975, *Med. Biol.* 53:331; Vargin, V. v. and B. F. Semenov, 1986, *Acta Virol.* 30:303; Venugopal, K. et al., 1994, *Res. Vet. Sci.* 57:188). In contrast, unimmunized animals are uniformly killed by challenge with RSSE or CEE. Additionally, either CEE or RSSE immunized mice were able to survive challenge with either CEE or RSSE, indicating homologous and heterologous protection as a result of vaccination. It is expected that cross-protection against other strains of TBE-causing viruses would be achieved (Holzmann, H. et al., 1992, Vaccine, 10, 345–349).

Generally, the DNA vaccine administered may be in an amount of about 1–5 ug of DNA per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

The vaccine may be given in a single dose schedule, or preferably a multiple dose schedule in which a primary course of vaccination may be with 1–10 separate doses, followed by other doses given at subsequent time intervals required to maintain and or reinforce the immune response, for example, at 1–4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, or other schedules sufficient to elicit the desired immune responses expected to confer protective immunity, or reduce disease symptoms, or reduce severity of disease.

In another embodiment, the present invention provides reagents useful for carrying out the present process. Such reagents comprise a DNA fragment containing prM/E gene from either RSSE or CEE or both RSSE and CEE, and a small, inert, dense particle. The DNA fragment, and dense particle are those described above.

Preferably, the DNA is frozen or lyophilized, and the small, inert, dense particle is in dry powder. If a coating solution is used, the dry ingredients for the coating solution may be premixed and premeasured and contained in a container such as a vial or sealed envelope.

The present invention also provides kits which are useful for carrying out the present invention. The present kits comprise a first container means containing the above-described frozen or lyophilized DNA. The kit also comprises a second container means which contains the coating solution or the premixed, premeasured dry components of the coating solution. The kit also comprises a third container means which contains the small, inert, dense particles in dry powder form or suspended in 100% ethanol. These container means can be made of glass, plastic or foil and can be a vial, bottle, pouch, tube, bag, etc. The kit may also contain written information, such as procedures for carrying out the present invention or analytical information, such as the amount of reagent (e.g. moles or mass of DNA) contained in the first container means. The written information may be on any of the first, second, and/or third container means, and/or a separate sheet included, along with the first, second, and third container means, in a fourth container means. The fourth container means may be, e.g. a box or a bag, and may contain the first, second, and third container means.

Other features of the invention will become apparent in the course of the following descriptions of exemplary embodiments which are given for illustration of the invention and are not intended to be limiting thereof.

The following materials and method were used in the examples below.

MATERIALS AND METHODS

Viruses, cells, media. Viruses were kindly provided by Dr. Robert Shope, Yale Arbovirus Research Unit, New Haven, Conn. Cell lines were obtained from the American Type Culture Collection. Central European encephalitis virus, strain Hypr, was isolated originally in 1953 from a TBE patient in Czechoslovakia. Russian spring summer encephalitis virus, strain Sofjin, was isolated originally in 1937 from a TBE patient from the Far Eastern USSR. Langat virus was isolated originally in 1956 from ticks collected in Malaysia (Calisher, C. H., 1988, *Acta Virol.* 32:469). RSSE and CEE viruses were propagated in VERO E6 cells and Langat virus was propagated in LLC-MK$_2$ cells. Cells were maintained in Eagle's minimal essential medium (EMEM) supplemented with 10% fetal bovine serum and antibiotics. Propagation and assay of RSSE or CEE viruses were carried out in a biosafety level 4 laboratory.

Cloning of the prM/E genes of RSSE and CEE. For reverse transcription and polymerase chain reaction (RT-PCR) amplification of the prM and E genes of RSSE and CEE viruses, specific oligonucleotide primers were designed to correspond to sequences previously reported for RSSE and CEE viruses (Genbank U39292, X03870). For the forward primers, nucleotides were modified around the translation initiation codon (bold type below) to generate sequences with a favorable context for translation initiation (Kozak, M., 1989, *J. Cell. Biol.* 108:229). The forward and reverse primers for RSSE were: 5'GCAGTAGACAG-GATGGGTTGGTTG3' (SEQ ID NO:3) and 5'GCACAGC-CAACTTAAGCTCCCACTCC3' (SEQ ID NO:4). The forward and reverse primers for CEE virus were: 5'GCGACGGACAGGATGGGCTGGTTGCTAG3' (SEQ ID NO:5), and 5'CACAGCGCAGCCAACTTACGC-CCCCACTCC3' (SEQ ID NO:6).

Total intracellular RNA of virus-infected Vero cells was extracted by using Trizol reagent (Gibco). For reverse transcription of the RSSE and CEE prM and E genes, the specific oligonucleotide primers, and/or random primers were used with Superscript cDNA synthesis reagents (Gibco). The same specific primers were used to amplify the cDNA by PCR, using Expand HiFi reagents (Boehringer Mannheim). PCR was carried out in a PCR 9600 thermocycler (Perkin Elmer). PCR conditions were 40 cycles of 94° C. for 40 sec, 38° C. for 45 sec, 72° C. for 1 min, after which reactions were incubated at 72° C. for 5 min and then held at 4° C. until used for cloning into the pCRII plasmid (Invitrogen). After verification of orientation, the cDNA inserts were excised from pCRII by digestion with EcoRV and SpeI or by digestion with NotI and partial digestion with BamHI. The RSSE and CEE cDNAs were then cloned into the HindIII (blunt), and NheI sites of pJW4303 (Lu, S. et al., 1996, *J. Virol.* 70:3978) or the NotI and BamHI sites of pWRG7077.

Transient expression assays of RSSE and CEE prM and E geues. For each assay, 5 $\mu$g of pWRG7077 containing RSSE or CEE prM and E genes, or control plasmid with no insert, was mixed with 200 $\mu$l of OptiMEM medium (Gibco) with no antibiotics. A separate solution was prepared consisting of 40 $\mu$l of Lipofectin reagent (Gibco) in 200 $\mu$l of OptiMEM (Gibco). Both solutions were incubated at room temperature for 30–45 min, after which they were combined and incubation was continued at room temperature for 10–15 min. OptiMEM (1.6 ml) was then added to each assay and the solution was placed onto monolayers of COS cells, in 25 cm$^2$ flasks, that had been rinsed one time with 2 ml of serum-free EMEM. The cells were incubated for 7 h at 37° C., then the Lipofectin/DNA solution was removed and fresh OptiMEM with antibiotics was added and incubation was continued. At 26 h postinfection, the medium was removed from the cell cultures and replaced with EMEM without cysteine or methionine. After incubation for 1 h at 37° C., 200 $\mu$Ci of $^{35}$S Promix (methionine and cysteine, Amersham) was added to each flask and the cells were incubated for 4 h at 37° C. The radiolabeling medium was then removed and cells were lysed on ice with 1 ml of a buffer consisting of 10 mM Tris-HCL, pH 8.0, 1 mM EDTA, 0.5 M NaCl, 4% Zwittergent 3-14 (Calbiochem-Behring) and protease inhibitors (Boerhringer Mannheim). Cell nuclei were removed by centrifugation for 5 min at 12,000×g in a microcentrifuge. An aliquot (100 $\mu$l) of each supernatant was mixed with 5 $\mu$l of a hyperimmune mouse ascitic fluid to RSSE or CEE viruses. After incubation on ice overnight, 100 $\mu$l of 50% Protein A Sepharose (Sigma) in lysis buffer was added to each tube, and the samples were shaken at 4° C. for 30 min. The Sepharose beads were recovered by centrifugation in a microcentrifuge and were washed three times with lysis buffer, and one time with 10 mM Tris-HCl, pH 8.0. The beads were then boiled for 2 min in protein sample buffer and analyzed by SDS polyacrylamide gel electrophoresis (PAGE) as described previously (Arikawa, J. et al., 1989, *J. Gen. Virol.* 70:615).

Preparation of gene gun cartridges, immunization and challenge of mice. Plasmid DNA was precipitated onto the outside surface of gold beads (approximately 2 $\mu$M in diameter) as described previously (Eisenbraun, M. D. et al., 1993, supra). The DNA loads were 0.5–1 µg/mg gold. The DNA-coated gold particles were dried on the inside walls of Tefzel tubing (McMaster Carr), which was then cut into 0.5 inch sections to make cartridges for the gene gun (Pertmer, T. M. et al., 1995, Vaccine 13:1427). These cartridges each contained approximately 0.5 mg of gold coated with 0.25–0.5 µg of DNA. BALB/c mice (approximately 6 to 8 wk-old) were immunized by using the hand-held, helium powered PowderJect-XR™ gene gun (Patent WO 95/19799) to deliver approximately 0.5–1 µg of DNA to the epidermis as described in Results and as reported previously (Pertmer, 1995, supra). For challenge studies, mice were transferred to a biosafety level 4 containment area and challenged by intraperitoneal inoculation of approximately 50 PFU of suckling mouse brain-passaged RSSE or CEE virus, a dose previously determined to be approximately 100 $LD_{50}$ for BALB/c mice. Mice were observed daily for signs of illness and for death.

ELISA. Direct IgG ELISA was performed by using methods similar to those described previously (Chu, Y.-K. et al., 1994, Virology 198:196; Meegan, J. M. et al., 1987, Am. J. Vet. Res. 48:1138). The viral antigen was prepared by detergent lysis of RSSE or CEE virus-infected VERO cells and infectious virus was inactivated by gamma irradiation of lysates (Chu, 1994, supra). One half of a 96-well polyvinylchloride (PVC) microtiter plate (Dynatech, Vienna, Va.) was coated directly with 100 µl/well of viral antigen diluted in 0.01 M PBS (pH 7.4) with 0.01% thimerosal (coating buffer) at a predetermined optimal dilution (1:1000). The other half was coated with 100 µl/well of a similarly treated negative antigen made from uninfected cells. Plates were wrapped in plastic wrap and incubated at 4° C. overnight. The next day plates were washed three times with wash buffer (coating buffer and 1% Tween-20; 300 µl/well/wash) by using an automatic plate washer (Biotek Instruments). All subsequent reagents added to the plates were diluted in wash buffer containing 5% skim milk (Difco). After the addition of each reagent, the plates were incubated in a moist environment at 37° C. for 1 h and then washed three times. Serum samples were initially diluted in microtiter tubes (Bio-Rad) and then further diluted from the microtiter tube into both positive and negative coated wells (final dilution of 1:100). Sera were screened at a 1:100 dilution or were serially diluted fourfold from 1:100 to 1:6400 in the ELISA plate. The positive control sera used were ascitic fluids from hyperimmunized mice inoculated with authentic homologous virus. Negative control sera used were prebleeds and controls from mice used in the study. After incubating, plates were washed and 100 µl of horseradish peroxidase (HRPO)-labeled goat anti-mouse IgG antibody (Boehringer Mannheim) (200 ng/ml) was added to each well. The substrate 2,2'-azino-di 3-ethybenthiazoline sulfonate (ABTS; Kirkegaard and Perry) was added, and plates were read at 410 nm with a Dynatech MR5000 reader and Lotus Measure. The readings were adjusted by subtracting the optical density (OD) of the negative antigen-coated wells from the positive antigen-coated wells. OD cutoff values were determined as follows: The mean of the adjusted OD values was determined for all the mouse prebleed and control samples and the standard deviation calculated. The cutoff of the assay was the mean OD value plus three standard deviations rounded up to the nearest tenth. An OD value was considered positive if it was greater than or equal to this value. The titer was equal to the reciprocal of the last dilution that was above or equal to the OD cutoff value. A serum sample was considered positive if the titer was ≧1:100.

Plaque-reduction neutralization assays ($PRNT_{80}$). Two-fold dilutions of sera (1:20–1:640) were prepared in EMEM supplemented with 10% FBS, and antibiotics. Dilutions were incubated at 56° C. for 30 min to inactivate complement, then were mixed with an equal volume of infectious RSSE or CEE virus in EMEM supplemented with 10% FBS and antibiotics to yield a mixture containing approximately 500 PFU of virus/ml. The virus/antibody mixtures were incubated at 37° C. for 1 h, and then stored at 4° C. overnight. The following day, 0.2 ml of the mixture was added to duplicate wells of six-well plates containing confluent monolayers of VERO E6 cells. The plates were incubated for 1 h (rocking gently every 15–20 min). The wells were then overlaid with 2 ml of 0.6% Seakem ME agarose (FMC Corp.) prepared in EMEM and supplemented with 5% FBS, nonessential amino acids, L-glutamine and antibiotics. The plates were incubated at 37° C. in 5% $CO_2$ for 6 days, after which a second overlay of 0.5% agarose in EMEM supplemented with 2.5% FBS and neutral red was applied. Plaques were visible 1 to 2 days later. The neutralizing antibody titer was calculated as a reciprocal of the highest dilution, resulting in a 80% reduction of plaques when compared to a control of virus with no added antibody.

Radiolabeling and immune precipitation of Laugat virus proteins. Conditions for infection and radiolabeling of Langat virus proteins with $^{35}$S-methionine were described previously (Iacono-Connors, L. et al., 1996, Virus Res. 43:125). Briefly, Langat virus-infected $LLC-MK_2$ cell monolayers in 25 $cm^2$ flasks were radiolabeled 18–24 h after infection with 200 µCi/ml of $^{35}$S-ProMix. The cells were lysed in a buffer consisting of 400 mM NaCl, 50 mM Tris HCl, pH 8.0, 1 mM EDTA, 1% Triton X-100, 0.2% deoxycholate, and protease inhibitors. Cell nuclei were removed by centrifugation. Langat virus proteins were immune-precipitated with 2–5 µl of experimental mouse sera and analyzed by SDS-PAGE.

EXAMPLE 1

Cloning and transient expression of prM and E genes.

Figure 2:
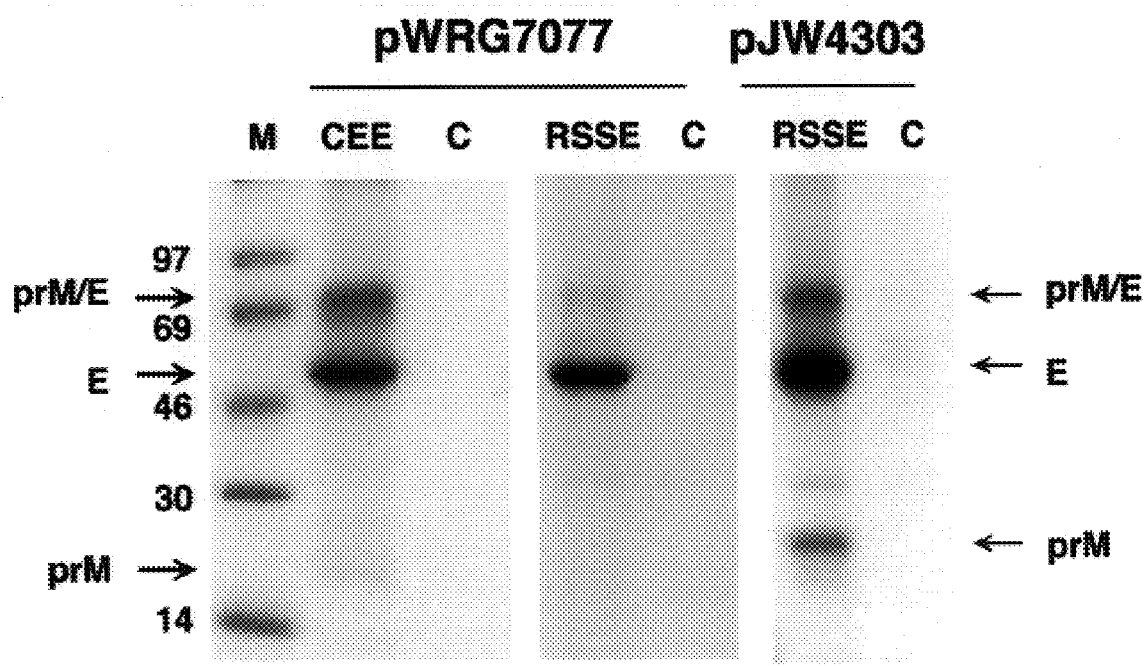
FIG. 2. Transient expression of naked DNA plasmids in COS cells. Plasmids containing the RSSE or CEE prM and E genes or plasmids with no inserted gene (C) were transfected into COS cells and expression products were immune precipitated with antibodies to RSSE or CEE viruses. Products were analyzed by PAGE and autoradiography. The positions of E, prM and uncleaved prM and E are indicated. The sizes (kD) of molecular weight markers (M) are shown.

Expression of the prM and E genes of RSSE and CEE were assayed by transfection of plasmids pJW4303 (Lu, S. et al., 1996, J. Virol. 70:3978) or pWRG7077 (FIG. 1) containing the RSSE genes, or pWRG7077 containing the CEE genes, into cell cultures. Each of the constructs produced E, prM and uncleaved prM/E which could be immune-precipitated with antibodies to authentic viral proteins (FIG. 2).

EXAMPLE 2

Antigenicity of the candidate vaccines.

BALB/c mice were immunized by delivery of DNA-coated gold beads to the abdominal epidermis by particle bombardment with helium pressure using the Accell™ gene gun (Geniva, Madison, Wisc.). For our first experiment and the first immunization of the second experiment, we used RSSE prM/E cloned into pJW4303 (Lu, 1996, supra). For all subsequent studies we used RSSE or CEE prM/E cloned into pWRG7077 (FIG. 1). The two plasmids have the same control elements; i.e., a human cytomegalovirus early promoter and intron A, and a bovine growth hormone polyadenylation/transcription termination signal. However, pWRG7077 does not contain the SV40 virus origin of replication and it has a kanamycin resistance gene rather than an ampicillin resistance gene and is therefore more suitable for the development of human vaccines.

Figure 3B:
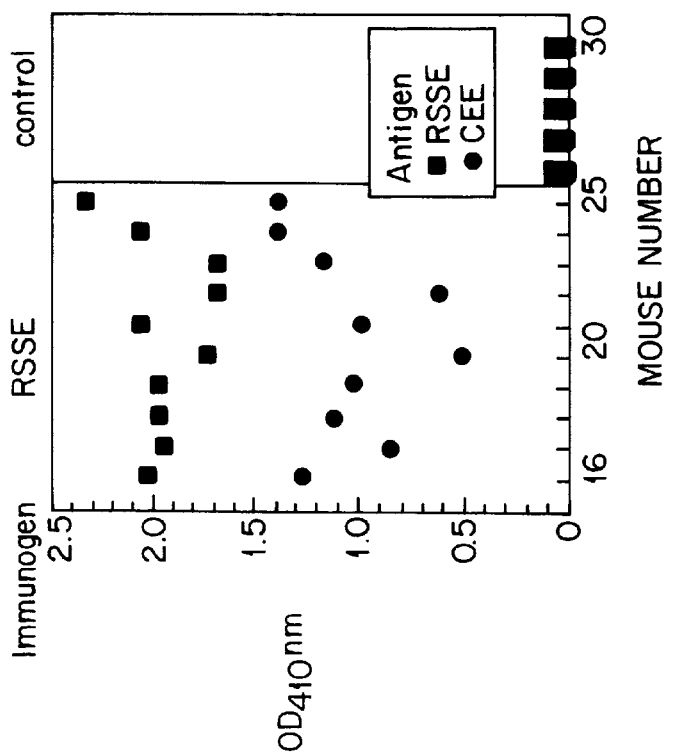
FIGS. 3A and B. Antibody responses of mice to naked DNA vaccines as detected by ELISA.
Figure 3A:
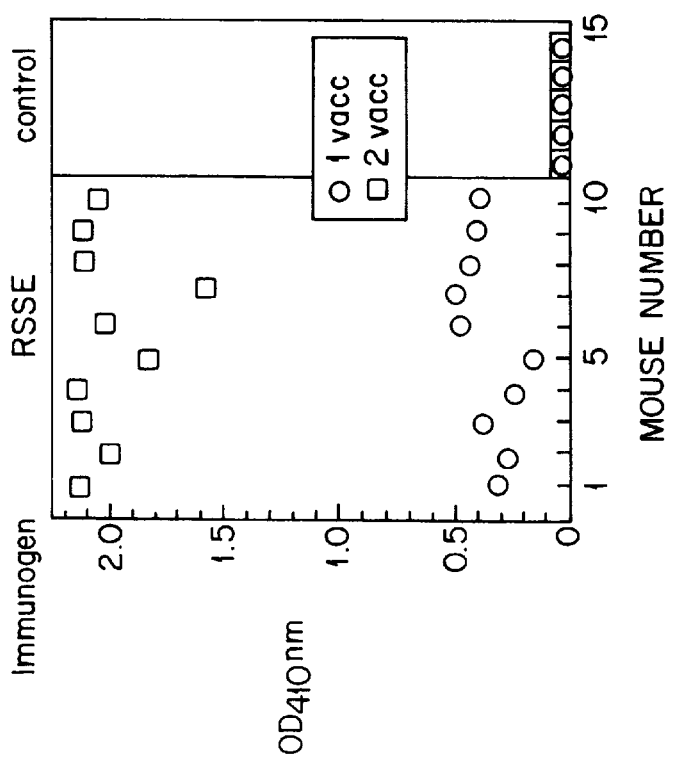

In our initial experiment, 10 mice were immunized with the RSSE construct and five mice were immunized with pJW4303 with no insert. Each mouse received two shots in adjacent sites with a combined total of approximately 1 μg of DNA. Four wk after the first immunization, the mice were bled and a second immunization of two shots was given. Four wk after the second immunization, the mice were bled again and sera were assayed by ELISA. All of the mice vaccinated with the RSSE construct had detectable responses to RSSE after one vaccination and all of them had increased responses after the second vaccination (FIG. 3A). None of the serum samples from the control mice displayed any reactivity with RSSE antigen (FIG. 3A).

To assess the ability of the RSSE DNA to elicit an antibody response to CEE virus, we performed a second experiment in which 10 mice were immunized as before with RSSE DNA and five mice were immunized with plasmid with no insert. Four wk after the second vaccination, ELISA was performed using RSSE or CEE antigen. Antibody responses were detected to both antigens with sera from all vaccinated mice (FIG. 3B).

To further evaluate the ability of the RSSE and CEE DNAs to elicit cross-reactive antibody responses, we performed a third experiment, in which we immunized 20 mice with RSSE DNA, 16 mice with CEE DNA, 16 mice with both RSSE and CEE DNA, and 18 mice with plasmid with no insert. As before, two immunizations (each consisting of two gene gun shots) were given at 4-wk intervals, but the DNA dose was reduced from 1 μg to 0.5 μg at each immunization. The mice were bled 4 wk after the second immunization and serum samples assayed by ELISA. Unexpectedly, we found that although there was an initial response to the antigen, there was not a rise in response after the second immunization (not shown). From other experiments, we knew that 0.5 μg of these DNAs were sufficient to elicit antibody responses in mice (not shown). Based on these results and those of other studies (not shown) we determined that a hardware modification to the gene gun (a brass insert which altered the helium flow and was intended to more evenly disperse the gold beads at the target inoculation site) resulted in reduced antigenicity. Consequently, we immunized the mice once more (4 wk after the second immunization) with the RSSE, CEE or RSSE, and CEE DNAs. The mice were then bled, and ELISA titers of sera determined on both RSSE and CEE antigen plates. ELISA with RSSE antigen resulted in antibody titers of 100 to $\geq 6400$ (FIG. 4). The CEE antigen used to coat the ELISA plates was apparently not as concentrated as the RSSE antigen, in that titers were uniformly lower with sera from both RSSE and CEE DNA-immunized mice (FIG. 4).

EXAMPLE 3

Protective efficacy of the candidate vaccines.

To determine if the DNA vaccines could protect mice from challenge with virulent RSSE and CEE viruses, mice from each of the three experiments described above were challenged either with virulent RSSE or CEE viruses. Some of the mice intended as controls for the RSSE cross-challenge of CEE-vaccinated mice (experiment three, above) were inadvertently vaccinated once with RSSE and CEE DNA. Thus, although all of the vaccinated mice survived challenge with RSSE virus, so did all but one of the controls. Therefore, despite our finding that these mice were clearly immunized, as indicated by their high-titered ELISA and $PRNT_{80}$ antibody responses (FIG. 4 and 5), we considered this experiment to be invalid with respect to protection and have not included these findings in the statistical analysis of protection (Table 1). To complete the cross-protection study, we vaccinated a fourth group of 10 mice, two times with 0.5 μg of CEE DNA. These mice and nine unvaccinated mice were then challenged with RSSE virus. Of these, all of the controls died, and all of the vaccinated mice survived.

A summary of the results from the series of four challenge experiments are shown in Table 1. All 55 of the mice immunized with plasmids containing the RSSE or CEE genes remained healthy after virus challenge. In contrast, all 27 control mice (18 immunized with plasmid lacking an insert, and nine unimmunized mice) displayed symptoms of infection after virus challenge; 14 of 17 mice died after challenge with RSSE virus, and eight of 10 mice died after challenge with CEE virus.

TABLE 1

Mortality of mice immunized with RSSE, CEE, or RSSE and CEE naked DNA vaccines and challenged with RSSE or CEE viruses

| | | No. dead/total no. | | | | | | |
|---|---|---|---|---|---|---|---|---|
| Virus(es) used | Challenge | Replicate 1 | | Replicate 2 | | Overall | | |
| for Vaccine | Virus | Vaccinated | Control | Vaccinated | Control | Vaccinated | Control | P[a] |
| CEE | CEE | 0/7 | 6/8 | | | 0/7 | 6/8 | 0.006 |
| CEE | RSSE | 0/10 | 9/9 | | | 0/10 | 9/9 | 0.00001 |
| RSSE | CEE | 0/5 | 2/2 | 0/10 | 6/8 | 0/15 | 8/10 | 0.0006 |
| RSSE | RSSE | 0/10 | 2/5 | 0/10 | 3/3 | 0/20 | 5/8 | 0.0003 |
| RSSE + CEE | CEE | 0/8 | 6/8 | | | 0/8 | 6/8 | 0.002 |

[a]Values determined with the test for homogeneity of odds ratios by using the StatXact-Turbo program from Cytel software Corp., Cambridge, MA.

EXAMPLE 4

Neutralizing antibody and sterile immunity.

Neutralizing antibodies correlate with protective immunity to tick-borne flaviviruses, as demonstrated in mice by passive transfer of neutralizing monoclonal antibodies to M and E (Heinz, F. X. et al., 1983, *Virology* 126:525; Iacono-Connors, 1996, supra). We measured the neutralizing antibody responses elicited by the vaccines in mice from the third experiment just before challenge. Because we found that CEE virus produced clearer, more easily discernible plaques than did RSSE virus, and because infectious virus assays required biosafety level 4 containment, we performed all $PRNT_{80}$ only with CEE virus. We found that all of the mice except one had prechallenge neutralizing antibody titers $\geq 40$ (FIG. 5). For samples in which an endpoint titer was reached, postchallenge neutralizing antibody titers were generally the same as or lower than prechallenge titers, suggesting a protection from infection (FIG. 5). For samples with prechallenge titers of ≥640, we also assayed pooled sera to estimate an endpoint titer. For the pooled serum samples from the CEE challenge group (109–116), the $PRNT_{80}$ titers were 1280 both before and after challenge. These results are also consistent with abortive infection by the challenge virus. The same results were obtained with postchallenge sera from the RSSE challenge group; i.e., the same or lower titers after challenge, but the results are not included in FIG. 5 because of the problem mentioned above with regard to invalid controls.

As another means to measure sterile immunity, we immune-precipitated radiolabeled Langat virus proteins with sera from mice vaccinated with RSSE or CEE DNAs both before and after challenge with RSSE or CEE viruses. Langat virus was used rather than RSSE or CEE viruses for these experiments because we previously demonstrated that Langat proteins are cross-reactive with RSSE and CEE antibodies (Iacono-Connors, 1996, supra) and because we were able to use Langat virus at biosafety level 3 containment rather than at level 4. We expected that vaccinated mice would have antibodies to Langat virus E, but not NS1. Postchallenge sera would also display reactivity only with E if the mice were not productively infected with the challenge viruses. If they were infected, however, we expected to also see reactivity with NS1. In addition to pooled samples, individual sera from mice 107 and 112 were assayed as representatives of samples for which a higher postchallenge than prechallenge PRNT titer was observed. Analysis of the immune precipitation products by PAGE revealed that although both E and NS1 proteins were clearly precipitated by polyclonal, hyperimmune mouse ascitic fluids to RSSE or CEE viruses, NS1 was not evident in any of the pre- or postchallenge sera from experimental mice (FIG. 6). The pooled sera from mice 109–116 did have a faint band in the area expected for NS1 (FIG. 6A), so these samples were assayed individually for reactivity with Langat virus proteins. None of these samples immune-precipitated Langat virus NS1 (FIG. 6C). Therefore, the immune-precipitation results and the PRNT results both suggest that sterile immunity was induced in the vaccinated mice.

TABLE 2

Antibody responses (geometric mean titers)[a] and duration of protective immunity elicited by the CEE DNA/gene gun vaccine administered with varying schedules and dosages

| Group | CEE1 | CEE2 | CEE3 | CEE4 | CEE5 |
|---|---|---|---|---|---|
| # vacc (interval) | 1 | 2 (4 wk) | 2 (4 wk) | 2 (8 wk) | 2 (12 wk) |
| Challenge | 8 wk | 8 wk | 24 wk | 24 wk | 24 wk |
| vacc 1 | 100 | <100 | 53.6 | 75.8 | nd |
| (range) | (<100–400) | (<100) | (<100–100) | (<100–100) | |
| vacc 2 | | 606 | 162.5 | 348.2 | 75.8 |
| (range) | | (400–1600) | (<100–400) | (100–1600) | (<100–100) |
| post | 4032 | 1600 | 2743 | 1600 | 800 |
| (range) | (1600–12800) | (400–6400) | (400–12800) | (400–6400) | (100–1600) |
| survival[b] | 9/9 | 10/10 | 9/10 | 10/10 | 4/5 |

[a]Geometric mean titers (GMT) for vacc 1 are from blood samples collected immediately before the subsequent vaccination; i.e. 8 wk, 4 wk, 4 wk, or 8 wk after the first vaccination for groups 1–4, respectively. GMT for vacc 2 are from blood samples collected immediately prior to challenge; i.e. 4 wk, 20 wk, 16 wk, or 12 wk after the second vaccination for groups 2–5, respectively.
[b]0/19 unvaccinated controls survived challenge

EXAMPLE 5

Duration of protective immunity after vaccination.

We examined the length of immunity induced by one or two vaccinations with approximately 0.5 μg of DNA given at varying intervals as described in Table 2. Individual sera were analyzed by ELISA and geometric mean titers (GMT) of each group were calculated for samples collected immediately before a subsequent vaccination, or immediately before challenge (Table 2). All mice that received one vaccination or two vaccinations 4 wk apart were protected from challenge at 8 wk after the first vaccination. Two vaccinations, given at 4, 8, or 12-wk intervals protected all but two mice from challenge 6 months after the initial vaccination (Table 2).

EXAMPLE 6

Primate studies

We have performed a comprehensive evaluation of DNA vaccines for RSSE and CEE viruses in mice (Schmaljohn, C. S. et al, 1997, *J. Virol.* 71:9563). We demonstrated that high levels of neutralizing antibodies to RSSE and CEE viruses can be elicited with two vaccinations, given 4 weeks apart, with 1 mg of PrM/E DNA. We further demonstrated that a single vaccination protected all mice from challenge 8 weeks later. Two immunizations given at an 8 week interval protected 10/10 mice from challenge 6 months after the first vaccination. Two vaccinations given at a 4 week interval protected 9/10 mice 6 months after the first vaccination, and 10/10 mice challenged 1 year after the initial vaccination. From our studies we conclude that we can achieve both homologous and heterologous protection of mice from challenge with RSSE and CEE viruses with either of the 2 DNA vaccines. Following these successes in mice and prior to human trials, we show that neutralizing antibodies are present following vaccination in rhesus macaques.

RSSE and CEE virus infection of primates: There is no known satisfactory disease model for TBE in monkeys. Studies performed at USAMRIID (Kenyon, R. H. et al., 1992, *Microb. Pathog.* 13:399) in Bonnet monkeys (*Macaca radiata*) demonstrated disease upon infection with some viruses in the TBE complex, but not consistently with RSSE or CEE viruses. Several studies, however, have demonstrated that rhesus macaques (*Macaca mulatta*) are useful antigenicity and immunogenicity models. In one study, rhesus monkeys were used to evaluate the efficacy and safety of a commercial killed vaccine (Hambleton, P. et al., 1983, *Infect. Immun.* 40:995). Vaccinated monkeys exposed intravenously developed a subclinical infection with no histopathological lesions but with transient clinical serum chemistry changes that included elevated aspartate aminotransaminase, lactate dehydrogenase, and creatine kinase activities. These chemical abnormalities declined as an immune response developed. The immune response was detected as neutralizing antibody in serum. Antibodies to viral envelope protein and two other infected cell-specific polypeptides were also detected.

To evaluate the immunogenicity of our vaccine, rhesus monkeys were randomized into five groups of four animals each. Group 1 was immunized with the genes that encode prM/E of CEE virus. Group 2 was immunized with RSSE virus prM/E genes. Group 3 animals received both RSSE and CEE prM/E genes. Group 4, the positive control, received the licensed Immuno TBE vaccine. Group 5 animals were vaccinated with the DNA carrier plasmid (WRG7077) without any gene inserts and served as the negative control. DNA vaccinated animals in groups 1, 2, and 5 were immunized with approximately 10 ug of DNA on days 0, 28, and 56. This was administered as four gene gun shots to the skin of the lower abdomen on each of the three immunization dates. Group 3 animals received approximately 20 ug of DNA consisting of four gene gun shots of RSSE and of CEE on each vaccination day. Group 4 received the Immuno vaccine, given at the human dose of 0.5 ml IM in the upper arm on days 0, 18, and 56. Monkeys were bled immediately prior to each vaccination and at day 70 to determine the antibody response by enzyme-linked immunosorbent assay (ELISA). Neutralizing antibody levels were determined by plaque reduction.

After 3 immunizations, sera from monkeys receiving the combination of RSSE and CEE DNA vaccines had ELISA titers (on RSSE and CEE antigens) and neutralizing antibody titers (to CEE virus) equivalent to those elicited by the licensed Austrian vaccine (FIG. 7). Neutralizing antibody levels ($PRNT_{80}$) to CEE virus were less than 1:40 for all prevaccination sera and were >1:1280 for all final bleeds, except for 1 (monkey H7T who had a 1:640 titer). Neutralizing antibody responses to RSSE virus were not measured because all assays with infectious RSSE virus and CEE virus require biosafety level 4 containment and it is technically more difficult to assay RSSE virus using a plaque reduction method than to assay CEE virus.

Because neutralizing antibodies are known to be a correlate of protective immunity, these studies indicate that it is likely that the DNA vaccine will protect humans from tick-borne encephalitis caused by RSSE and CEE.

DISCUSSION

The use of nucleic acid vaccines to elicit protective immunity to a variety of viruses has been demonstrated in numerous experimental models (for reviews see Ulmer, J. B. et al., 1996, *Adv. Exp. Med. Biol.* 397:49; Ulmer, J. B. et al., 1995, *Ann. NY Acad. Sci.* 772:117; Ulmer, J. B. et al., 1996, *Curr. Opin. Immunol.* 8:531; Whalen, R. g., 1996, *Emrg. Infec. Dis.* 2:168). In the studies reported here, gene gun administration of microgram quantities of DNA encoding the prM and E genes of RSSE or CEE viruses was effective for inducing homologous and heterologous protective immunity in mice. We designed our candidate vaccines to take advantage of earlier findings that showed that coexpressing prM and E results in the formation of secreted, antigenic and immunogenic subviral particles (Heinz, F. X. et al., 1995, *Vaccine* 13:1636; Konishi, E. and P. W. Mason, 1993, *J. Virol.* 67:1672; Konishi, E. et al., 1992, *Virology* 190:454; Konishi, E. et al., 1992, *Virology* 188:714; Pincus, S. et al., 1992, *Virology* 187:290). Such subviral particles, consisting of heterodimers of prM and E, are also a by product of normal flavivirus morphogenesis; i.e., the so-called "slowly sedimenting hemagglutinins" (SHA) (Heinz, F. and C. Kunz, 1977, *Acta Virol.* 21:308; Mason, P. W. et al, 1991, *Virology* 180:294; Russell, P. K. et al., 1980, In R. w. Schlesinger (ed.) *The Togaviruses.* Academic Press-:New York, p. 503–529). The enhanced immunogenicity of these particles is in part due to the inability of E to assume a native conformation in the absence of prM (Konishi, E. and P. W. Mason, 1993, supra). So, although passively transferred neutralizing monoclonal antibodies to E can protect animals from subsequent flavivirus challenge (Buckley, A. and E. A. Gould, 1985, supra; Gould and Buckley, 1986, supra; Heinz, F. X. et al., 1983, supra; Iacono-Connors et al., 1996, supra; Kaufman, B. M. et al., 1987, supra; Kimura-Kuroda, J. and K. Yasui, 1988, supra; Mason et al., 1989, supra; Mathews and Roehrig, 1984, supra), active immunization with expressed, soluble E is not as efficient as prM and E together for inducing protective immunity (Heinz et al., 1995, supra).

As indicated above, neutralizing antibodies to E are, by themselves, sufficient to protect mice, and presumably humans, from CEE virus. Thus, although DNA vaccines delivered to the epidermis by gene gun inoculation efficiently induce both cell-mediated and humoral immune responses (Haynes et al., 1994, supra; Pertmer et al., 1995, supra), we were most interested in analyzing the induction of neutralizing antibodies as a correlate of protection. Our vaccination strategy of two immunizations of 0.5 to 1 $\mu$g of DNA delivered at 4-wk intervals was based on optimal parameters determined for gene gun inoculation of a reporter gene (Eisenbraun et al., 1993, supra). In those studies, it was determined that microgram quantities of DNA were sufficient for maximal protein expression and eliciting antibodies to the expression product. Increasing the amount of DNA from 0.1 to 5 $\mu$g of DNA per mg of gold did not result in higher expression levels and it was suggested that the 300 copies of DNA found on a typical gold bead (0.1 $\mu$g DNA/mg gold) are all that a single cell can efficiently express (Eisenbraun et al., 1993, supra). Although we did not test lesser amounts of DNA, we did investigate other immunization schedules. Our finding that one vaccination with 0.5 $\mu$g of DNA can protect mice for at least 2 months, and two vaccinations can protect for at least 6 months suggests that the immune response generated is long-lived and offers encouragement for further development of this vaccine for human use.

The RSSE and CEE cross-reactive immunity that we observed was not surprising in that the prM and E polyprotein expression products of the two viruses are 94% identical. Nevertheless, it is known that certain E-specific monoclonal antibodies differentiate RSSE and CEE viruses, and that minor changes in E can result in altered neuroinvasiveness in mice (Holzmann et al., 1997, *J. Gen. Virol.* 78:31, supra; Holzmann et al., 1992, *Vaccine* 10:345). Consequently, although either of our DNA vaccines by itself may be sufficient for immunity to TBE-causing flaviviruses, it may be prudent to include both DNAs in a vaccine developed for humans.

In some of our experiments, not only did our candidate vaccines protect mice from death and illness after challenge, but apparently prevented replication of the challenge virus, as indirectly measured by the absence of antibody titer increases and the absence of NS1-specific antibodies after challenge. Of course, neither of these methods is sensitive enough to detect low levels of virus replication, so it is possible that the challenge virus did establish an infection but was quickly eliminated. If sterile immunity did occur, we assume that it was related to neutralization of the challenge virus by circulating antibodies. Among the mechanistic possibilities for this are prevention of adsorption of virus to host cell receptors, inhibition of fusion of the viral envelope to the host plasma membrane, or alteration of the conformation of the viral envelope proteins to perturb entry of the virus into the host cell (Dimmock, N. J., 1995, *Med. Virol.* 5:165). Whichever mechanism occurred, sterile immunity was apparently not required for protective immunity. This is evidenced by the large increases in antibody titers after challenge of some of the mice in our duration of immunity experiments. Additionally, we show that monkeys receiving the DNA vaccine had ELISA titers on RSSE and CEE antigens and neutralizing antibody titers to CEE virus equivalent to the commercially available inactivated virus vaccine. Since neutralizing antibodies correlate with protective immunity, the DNA vaccine described here is likely to protect humans from tick-borne encephalitis caused by RSSE and CEE.

In conclusion, we feel that the DNA/gene gun technology offers great promise for a new generation of vaccines for TBE. The technology is still new and is undergoing constant modifications and revisions. Nevertheless, gene gun immunization of other DNAs, in quantities similar to those in our studies, effectively induced immune responses in larger animals such as pigs and non-human primates after gene gun inoculation (Fuller, 1995, supra; Fuller, D. H. et al., 1996, *J. Med. Primatol.* 25:236). Thus, we expect that the amount of DNA needed for successful vaccination will not present a technical barrier. Also, because gene gun delivery of a candidate virus vaccine for hepatitis B (Geniva) was recently approved for use in a human clinical trial, we anticipate no regulatory obstacles for its eventual use in TBE vaccines for humans.

What is claimed is:

1. A method for inducing a protective immune response to a tick-borne flavivirus protein in a mammal, comprising (i) preparing a nucleic acid encoding an antigenic determinant of a tick-borne flavivirus prM/E protein operatively linked to a CMV promoter operative in cells of a mammal, which nucleic acid is suitable for stably producing the antigenic determinant in a mammal;

(ii) coating the nucleic acid in (i) onto carrier particles;

(iii) accelerating the coated carrier particles into epidermal cells of the mammal in vivo; and (iv) inducing a protective immune response in said mammal upon exposure to a tick-borne flavivirus.

2. The method according to claim 1 wherein the carrier particles are gold.

3. The method according to claim 1 wherein the tick-borne flavivirus prM/E protein is selected from the group consisting of Russian spring summer encephalitis prM/E proteins, and Central European encephalitis prM/E proteins.

4. The method according to claim 1 wherein the nucleic acid encodes a protein coding region comprising SEQ ID NO:1.

5. A method for inducing a protective immune response to a tick-borne flavivirus protein in a mammal, comprising (i) preparing a nucleic acid encoding an antigenic determinant of a Russian spring summer encephalitis tick-borne flavivirus prM/E protein operatively linked to a promoter operative in cells of a mammal, which nucleic acid encodes a protein coding region comprising SEQ ID NO:2 and is suitable for stably producing the antigenic determinant in a mammal;

(ii) coating the nucleic acid in (i) onto carrier particles;

(iii) accelerating the coated carrier particles into epidermal cells of the mammal in vivo; and (iv) inducing a protective immune response in said mammal upon exposure to a tick-borne flavivirus.

6. The method according to claim 1 wherein the nucleic acid encodes a protein coding region comprising SEQ ID NO: 1 and SEQ ID NO:2.

7. A kit for inducing a protective immune response to a tick-borne flavivirus protein in a mammal, comprising packaged in association:

(a) a nucleic acid encoding an antigenic determinant of a tick-borne flavivirus prM/E protein operatively linked to a CMV promoter operative in cells of a mammal, which nucleic acid is suitable for stably producing the antigenic determinant in a mammal;

(b) one or both of a coating solution and/or components of a coating solution; and (c) carrier particles.

8. The kit of claim 7, wherein the tick-borne flavivirus prM/E protein is selected from the group consisting of Russian spring summer encephalitis prM/E proteins, and Central European encephalitis prM/E proteins.

9. The kit of claim 7, wherein the nucleic acid encodes a protein coding region comprising SEQ ID NO:1.

10. The kit of claim 7, wherein the nucleic acid encodes a protein coding region comprising SEQ ID NO:1 and SEQ ID NO:2.

11. A kit for inducing a protective immune response to a tick-borne flavivirus protein in a mammal, comprising packaged in association:

(a) a nucleic acid encoding an antigenic determinant of a Russian spring summer encephalitis tick-borne flavivirus prM/E protein operatively linked to a promoter operative in cells of a mammal which nucleic acid encodes a protein coding region comprising SEQ ID NO:2 and is suitable for stably producing the antigenic determinant in a mammal;

(b) one or both of a coating solution and/or components of a coating solution; and (c) carrier particles.

* * * * *

SEQUENCE LISTING

```
<160> NUMBER OF SEQ ID NOS: 6

<210> SEQ ID NO 1
<211> LENGTH: 2055
<212> TYPE: DNA
<213> ORGANISM: Central European Encephalitis virus
<220> FEATURE:
<223> OTHER INFORMATION: genomic

<400> SEQUENCE: 1
gcgacggaca ggatgggctg gttgctagtc attactctgt                     40
tggggatgac gattgctgca accgtgagga aagaaaggga                     80
cggctcaact gtgatcagag ctgaaggaaa ggacgcagca                    120
actcaggtgc gtgtggagaa tggcacctgt gtgatcctgg                    160
ctactgacat ggggtcatgg tgtgatgatt cactgtccta                    200
tgagtgtgtg accatagatc aaggagaaga gcctgttgac                    240
gtggattgtt tttgccggaa tgttgatgga gtctatctgg                    280
agtatggacg ctgtgggaaa caggaaggct cacggacaag                    320
gcgctcagtg ctgatcccat cccatgccca gggagagctg                    360
acggggaggg gacacaaatg gctagaagga gactcgctgc                    400
gaacacatct caccagagtt gagggatggg tttggaagaa                    440
caggctactt gccctggcga tggtcaccgt tgtgtggttg                    480
accctggaga gtgtggtgac cagggtcgcc gttctggttg                    520
tgctcctgtg tttggcgccg gtctacgctt cgcgttgcac                    560
acatttggaa aacagggact ttgtgactgg tactcagggg                    600
actacgaggg tcaccttggt gctggaactg ggtggatgtg                    640
ttaccataac agctgagggg aagccttcaa tggatgtgtg                    680
gcttgacgcc atttaccagg agaaccctgc tcagacacgt                    720
gagtactgtt tacacgccaa gttgtcggac actaaggttg                    760
cagccagatg cccaacaatg ggaccagcca ctttggctga                    800
agaacaccag ggtggtacag tgtgcaagag agatcagagt                    840
gatcgaggct ggggcaacca ctgtggactt tttggaaagg                    880
```

-continued

| | |
|---|---|
| gtagcattgt ggcctgtgtc aaggcggctt gtgaggcaaa | 920 |
| aaagaaagcc acaggacatg tgtacgacgc caacaaaata | 960 |
| gtgtacacgg tcaaagtcga accacacacg ggagactatg | 1000 |
| ttgccgcaaa cgagacacat agtgggagga agacggcatc | 1040 |
| cttcacagtt tcttcagaga aaaccattct gactatggt | 1080 |
| gagtatggag atgtgtctct gttgtgtagg gtcgctagtg | 1120 |
| gcgttgactt ggcccagacc gtcatccttg agcttgacaa | 1160 |
| gacagtggaa caccttccaa cggcttggca ggtccacagg | 1200 |
| gactggttta atgatctggc tctgccatgg aaacatgagg | 1240 |
| gagcgcgaaa ctggaataac gcagaaagat tggttgaatt | 1280 |
| tgggggctcct catgctgtca agatggatgt gtacaacctc | 1320 |
| ggagaccaga ctggagtgtt actgaaggct ctcgctgggg | 1360 |
| ttcctgtggc acacattgag ggaaccaagt accacctgaa | 1400 |
| gagtggccat gtgacctgcg aagtgggact ggaaaaactg | 1440 |
| aagatgaaag gtcttacgta cacaatgtgt gacaaaacaa | 1480 |
| agttcacatg gaagagagct ccaacagaca gtgggcatga | 1520 |
| tacagtggtc atggaagtca cattctctgg aacaaagccc | 1560 |
| tgtaggatcc cagtcagggc agtggcacat ggatctccag | 1600 |
| atgtgaacgt ggccatgctg ataacgccaa acccaacaat | 1640 |
| tgaaaacaat ggaggtggct tcatagagat gcagctgccc | 1680 |
| ccaggagaca acatcatcta tgttggggaa ctgagttatc | 1720 |
| aatggttcca aaagggagt agcatcggaa gagttttcca | 1760 |
| aaagaccaag aaaggcatag aaagactgac agtgataggg | 1800 |
| gagcacgcct gggacttcgg ttctgctgga ggctttctga | 1840 |
| gttcaattgg gaaggcgttg cacacggtcc ttggtggtgc | 1880 |
| tttcaacagc atcttcgggg gagtgggggtt tctaccaaag | 1920 |
| cttctattag gagtggcatt ggcttggttg ggcctgaaca | 1960 |
| tgagaaaccc tacaatgtcc atgagctttc tcttggctgg | 2000 |
| agttctggtt ttggccatga cccttggagt gggggcgtaa | 2040 |
| gttggctgcg ctgtg | 2055 |

<210> SEQ ID NO 2
<211> LENGTH: 2051
<212> TYPE: DNA
<213> ORGANISM: Russian spring summer encephalitis virus
<220> FEATURE:
<223> OTHER INFORMATION: genomic

<400> SEQUENCE: 2

| | |
|---|---|
| gcagtagaca ggatgggttg gttgctggtt gtttgtcctgt | 40 |
| tgggagtgac acttgcagcc acagtgcgga aggaaagaga | 80 |
| tggcaccacc gtgatcagag ctgaaggaaa agatgcggca | 120 |
| acccaggtgc gtgtgtggaaaa tggcacctgt gtgatcctgg | 160 |
| ccacggacat gggatcatgg tgtgatgatt cactaaccta | 200 |

-continued

| | |
|---|---|
| tgagtgtgtg accatagacc aggggggagga accggttgac | 240 |
| gtggattgct cttgcaggaa tgttgatgga gtttacctgg | 280 |
| agtatgggcg gtgtggaaaa caagaaggat caagaacaag | 320 |
| gcgttcagtg ctgatcccat cccacgctca gggagatctc | 360 |
| acaggaaggg gacacaaatg gttagaaggg gattcattac | 400 |
| ggacgcacct cactagagtt gagggatggg tctggaagaa | 440 |
| taaagtgctc accctggcgg tgatcgccgt tgtgtggctg | 480 |
| accgtggaaa gtgtggtgac tcgggtcgcc gtagtggtgg | 520 |
| tgctcttgtg cctggctccg gtttatgcct cacggtgcac | 560 |
| acatttggaa aacagggatt ttgttactgg cactcagggg | 600 |
| accactcgtg tgactctggt gttggaactg ggaggatgcg | 640 |
| tcaccataac agctgagggg aagccctcga tggatgtgtg | 680 |
| gcttgactcc atctaccagg agaaccctgc caagacacgt | 720 |
| gagtactgcc ttcacgcaaa actatcggat accaaagtcg | 760 |
| cggccaggtg cccaacaatg ggacctgcca ctttggctga | 800 |
| agagcaccag agcggcacag tgtgtaagag agaccagagt | 840 |
| gatcgaggct ggggcaacca ttgtggatta tttggaaaag | 880 |
| gcagcattgt gacctgtgtc aaggcgtctt gtgaggcaaa | 920 |
| aaagaaagcc acaggacacg tgtatgacgc taacaaaatt | 960 |
| gtgtacacag tcaaagtaga gccgcacacg ggggattacg | 1000 |
| tcgctgctaa tgagactcac agtggaagaa aaaccgcgtc | 1040 |
| cttcacggtt tcctcggaga ggaccatctt gaccatggga | 1080 |
| gactacggag acgtgtcctt gttatgcaga ctagccagcg | 1120 |
| gtgttgacct tgctcagacc gtcatcctgg agcttgacaa | 1160 |
| gacctcagaa cacctaccga cggcctggca ggtccaccgg | 1200 |
| gactggttca atgatctggc cctaccgtgg aaacatgaag | 1240 |
| gggcacagaa ttggaacaac gcggaacggc tggttgagtt | 1280 |
| tggagctcca catgctgtga aaatggacgt gtacaacctt | 1320 |
| ggagaccaga ctggagtgtt gctcaaatca cttgctggtg | 1360 |
| ttcctgtggc gcacattgat ggaaccaagt accacctgaa | 1400 |
| aagtggccac gtgacatgcg aggtaggact agaaaaactt | 1440 |
| aagatgaaag gtcttacata cacaatgtgt gacaagacga | 1480 |
| aattcacgtg caaaagaatt ccaacagaca gtggacatga | 1520 |
| cacagtggtc atggaagttg cgttctctgg gaccaaaccc | 1560 |
| tgcaggatcc cggtgagggc cgtggcacac ggctccccgg | 1600 |
| atgtgaacgt ggccatgttg atgacaccca accccacaat | 1640 |
| cgaaaacaat ggcggtggct tcatagaaat gcagttacct | 1680 |
| ccaggagata atatcatcta tgttgggaa ctgagtcacc | 1720 |
| aatggttcca aaaagggagt agcattggaa gggttttttca | 1760 |

| | |
|---|---|
| aaaaaccaga aaaggcatag aaaggctgac agtgatcgga | 1800 |
| gaacatgcct gggattttgg ctctactggt ggtttcctga | 1840 |
| cctcggttgg taaggcgctg cacacagttc ttggcggtgc | 1880 |
| ctttaacagc cttttggag gagtggggtt cttgcccaag | 1920 |
| atcctagtgg gagtggtcct ggcctggttg ggcctgaaca | 1960 |
| tgaggaatcc caccatgtcc atgagcttcc ttctggctgg | 2000 |
| aggactggtt ctggccatga cactcggagt gggagcttaa | 2040 |
| gttggctgtg c | 2051 |

<210> SEQ ID NO 3
<211> LENGTH: 24
<212> TYPE: DNA
<213> ORGANISM: Artificial
<220> FEATURE:
<223> OTHER INFORMATION: /note="PCR primer sequence derived from genomic sequence reported in GenBank X03870"

<400> SEQUENCE: 3
gcagtagaca ggatgggttg gttg                                    24

<210> SEQ ID NO 4
<211> LENGTH: 26
<212> TYPE: DNA
<213> ORGANISM: Artificial
<220> FEATURE:
<223> OTHER INFORMATION: /note="PCR primer sequence derived from genomic sequence reported in GenBank X03870"

<400> SEQUENCE: 4
gcacagccaa cttaagctcc cactcc                                  26

<210> SEQ ID NO 5
<211> LENGTH: 28
<212> TYPE: DNA
<213> ORGANISM: Artificial
<220> FEATURE:
<223> OTHER INFORMATION: /note="PCR primer sequence derived from genomic sequence reported in GenBank U39292"

<400> SEQUENCE: 5
gcgacggaca ggatgggctg gttgctag                                28

<210> SEQ ID NO 6
<211> LENGTH: 30
<212> TYPE: DNA
<213> ORGANISM: Artificial
<220> FEATURE:
<223> OTHER INFORMATION: /note="PCR primer sequence derived from genomic sequence reported in GenBank U39292"

<400> SEQUENCE: 6
cacagcgcag ccaacttacg cccccactcc                              30